United States Patent [19]

Trist et al.

[11] Patent Number: 5,486,514
[45] Date of Patent: Jan. 23, 1996

[54] CARBAMATE DERIVATIVES

[75] Inventors: David Trist; Giorgio Pentassuglia; Maria E. Tranquillini; Antonella Ursini, all of Verona, Italy

[73] Assignee: Glaxo SpA, Verona, Italy

[21] Appl. No.: 256,358

[22] PCT Filed: Jan. 15, 1993

[86] PCT No.: PCT/EP93/00099

§ 371 Date: Jul. 20, 1994

§ 102(e) Date: Jul. 20, 1994

[87] PCT Pub. No.: WO93/14075

PCT Pub. Date: Jul. 22, 1993

[30] Foreign Application Priority Data

Jan. 21, 1992 [GB] United Kingdom .................... 9201181

[51] Int. Cl.$^6$ .................... C07D 243/12; A61K 31/55
[52] U.S. Cl. .................... 514/221; 540/518
[58] Field of Search .................... 540/518; 514/221

[56] References Cited

FOREIGN PATENT DOCUMENTS 0376849  7/1990  European Pat. Off. ........... 540/575

*Primary Examiner*—Robert T. Bond
*Attorney, Agent, or Firm*—Bacon & Thomas

[57] ABSTRACT

The present invention relates to compound of formula (I) which are antagonists of gastrin and CCK-B receptors. The compounds of formula (I) are carbamate derivatives.

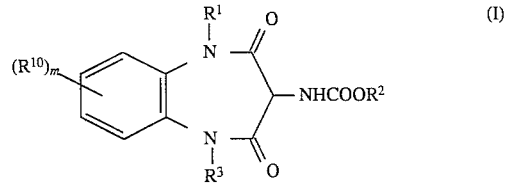

14 Claims, No Drawings

CARBAMATE DERIVATIVES

This application is a 371 of PCT/EP93/00099, filed Jan. 15, 1993.

This invention relates to novel 1,5-benzodiazepine derivatives, to processes for their preparation, to pharmaceutical compositions containing them and to their use in medicine.

In particular the invention relates to compounds which are potent and specific antagonists of gastrin and/or cholecystokinin (CCK).

Thus, the invention provides compounds of general formula (I)

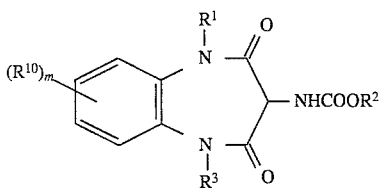

wherein $R^1$ represents a phenyl, $C_{3-7}$cycloalkyl, bridged $C_{7-11}$cycloalkyl or $C_{1-6}$alkyl group which alkyl group may be substituted by a hydroxy, phenyl, $C_{1-6}$alkoxycarbonyl, $C_{3-7}$cycloalkyl or bridged $C_{7-11}$cycloalkyl group or $R^1$ represents the group $XYR^4$ wherein X is a $C_{1-3}$ straight or branched alklene chain, Y is C=O, $C(OR^5)_2$ or $C(SR^5)_2$ and $R^4$ is a $C_{1-6}$alkyl, optionally substituted phenyl, $C_{3-7}$cycloalkyl or bridged $C_{7-11}$cycloalkyl.

$R^2$ represents a substituted or unsubstituted phenyl (wherein the substitutents may be 1 or 2 of halo, $C_{1-4}$alkyl, nitro, cyano, trifluoromethyl, trifluoromethoxy $C_{1-4}$alkylthio or $(CH_2)_n$ $R^6$ wherein $R^6$ is hydroxy, $C_{1-4}$alkoxy, $CO_2R^7$ or $NR^8R^9$.

$R^3$ represents phenyl optionally substituted by one or two halogen atoms;

$R^7$ represents hydrogen or a $C_{1-4}$alkyl group;

$R^8$ and $R^9$ independently represent hydrogen or a $C_{1-4}$alkyl group.

$R^{10}$ represents hydrogen or a halogen atom; m is zero, 1 or 2;

n is zero or 1; and pharmaceutically acceptable salts and solvates thereof.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) 'alkyl' when used as a substituent or part of a substituent group means that the group may be straight or branched. Thus, $C_{1-6}$alkyl includes methyl, ethyl, n-propyl, isopropyl, n-butyl, isobutyl or tert-butyl, n-pentyl, isopentyl neopentyl, n-hexyl, isohexyl, 1,3-dimethylbutyl, 3,3-dimethylbutyl, 2,3-dimethylbutyl.

For the group $R^1$ the term $C_{3-7}$cycloalkyl as a group or pan of a group refers to a monocyclic alkyl group such as cyclopropyl, cylobutyl, cyclopentyl, cyclohexyl or cycloheptyl. The term bridged $C_{7-11}$cycloalkyl refers to groups such adamantyl, norbornanyl or norbornenyl.

For the groups $R^7R^8$ and $R^9$ the term $C_{1-4}$alkyl includes 3-4-cycloalkyl (e.g. cyclopropyl or cyclobutyl) as well as straight or branched chain alkyl groups as defined above.

Halogen in the definition of compounds of formula (I) may represent a fluoro, chloro, bromo or iodo substituent.

When $R^2$ is a phenyl group substituted by a single substituent this may be in the ortho, para or more preferably in the meta position.

When $R^{10}$ is halogen this is preferably chlorine or fluorine.

When m is 1 or 2 the halogen atom(s) e.g. chlorine or fluorine are preferably in the 7 and/or 8 positions.

The compounds of formula (I) posses at least one asymmetric carbon atom (namely the carbon atom occupying the 3-position of the diazeine ring) and particularly preferred compounds of the invention or those having the relative stereochemistry shown in formula (1a)

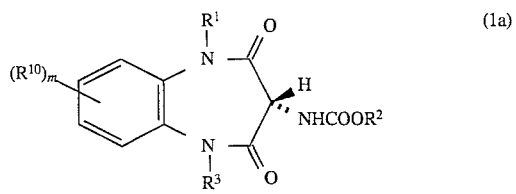

wherein the solid wedge bond indicates the group is above the plane of the diazepine ring and the broken bond indicates the group is below the plane of the diazepine ring.

When $R^1$ represents an alkyl group substituted by a hydroxyl group this is preferably a $C_{3-6}$alkyl group substituted by hydroxy. Examples of such groups include 2-hydroxypropyl, 2-hydroxy-3-methylbutyl and 2-hydroxy-3,3-dimethylbutyl 3-hydroxypropyl.

When $R^1$ represent an alkyl group substituted by a $C_{3-7}$cycloalkyl group this is preferably a $C_{2-3}$alkyl group such as ethyl substituted by a $C_{3-7}$cycloalkyl group such as cyclopentyl.

When $R^1$ is a bridged $C_{7-11}$cycloalkyl group this may be for example an adamantyl group such as 1-adamantyl or 2-adamantyl group or a 2-norbornanyl group.

When $R^1$ is an alkyl group substituted by a bridged $C_{7-11}$cycloalkyl group this is preferably an ethyl group or more especially a methyl group substituted by a bridged $C_{7-11}$cycloalkyl group. Examples of suitable bridged cycloalkyl groups include adamantyl such as 1-adamantyl or 2-adamantyl, 2-norbornanyl or 5-norbornenyl. Most preferably $R^1$ represents 1-adamantylmethyl.

When $R^1$ is alkyl substituted by phenyl this may be for example benzyl or phenethyl.

When $R^1$ is alkyl substituted by alkoxycarbonyl this is preferably methyl substituted by alkoxycarbonyl such methoxycarbonyl or t-butoxycarbonyl.

When $R^1$ is alkyl it is preferably $C_{4-6}$alkyl such as 3-methylbutyl or 3,3-dimethylbutyl.

When $R^1$ is the group $XYR^4$ a preferred class of compounds are those wherein X is a methylene group. A further preferred class of compounds are those wherein Y represents C=O.

A preferred class of compounds of formula (I) is that in which $R^1$ represents a bridged $C_{7-10}$cycloalkyl e.g. such as adamantyl, norbornanyl, $C_{4-6}$alkyl e.g. 3-methyl butyl or 3,3-dimethyl butyl, $C_{3-6}$ hydroxy alkyl e.g. 3-hydroxypropyl, 2-hydroxy-3-methylbutyl, 2-hydroxy-3,3-dimethylbutyl, $C_{1-2}$alkyl substituted by a bridged $C_{7-10}$cycloalkyl group e.g. 2-norbornanylmethyl, 5-norbornenylmethyl, 2-adamantylmethyl, 2-adamantylethyl, 2-(1-adamantyl)ethyl, 1-adamantylmethyl, alkoxycarbonylalkyl, e.g. methoxycarbonylmethyl or t-butyoxycarbonylmethyl, 2-cyclopentylethyl or the group $CH_2COR^4$ in which $R^4$ is $C_{3-4}$alkyl e.g. isopropyl or t-butyl, cyclopentyl, phenyl or adamantyl.

A particularly preferred class of compounds of formula (I) is that in which $R^1$ is 3-methylbutyl 3,3-dimethylbutyl, adamantylmethyl, $CH_2COCH(CH_3)_2$, or cyclopentylethyl.

A further preferred class of compounds of formula (I) is that in which $R^2$ represents phenyl optionally substituted by chlorine, fluorine, bromine, methyl, methoxy, dimethylamino or $(CH_2)_nCO_2R^7$ wherein $R^7$ is hydrogen methyl or ethyl. Most preferably $R^2$ represents phenyl optionally substituted by dimethylamino, methoxy, bromine, carboxyl or methoxycarbonyl.

A further preferred class of compounds of formula (I) is that in which $R^3$ represents phenyl or phenyl mono- or di-substituted by fluorine, preferably in the ortho and/or para position(s). Preferably $R^3$ represents unsubstituted phenyl or 2-fluorophenyl.

A preferred group of compounds of formula (I) are those wherein $R^3$ represents $C_{4-6}$6alkyl e.g. 3-methylbutyl or 3,3-dimethylbutyl, 3-hydroxypropyl, 2-cyclopentylethyl or adamantylmethyl; $R^2$ is phenyl optionally substituted by a bromine atom, dimethylamino, methoxy, carboxyl or methoxycarbonyl group; $R^3$ is phenyl optionally substituted by fluorine; $R^{10}$ is hydrogen, chlorine or fluorine and m is zero, 1 or 2.

A particularly preferred group of compounds of formula (I) are those wherein $R^1$ is 3-methylbutyl $R^2$ is phenyl optionally substituted in the meta position by dimethylamino, methoxy, bromine, methoxycarbonyl or carboxyl; $P^3$ is phenyl or orthofluorophenyl, $R^{10}$ is chlorine or fluorine at the 8 position or $R^{10}$ is chlorine at 7 and 8 positions or $R^{10}$ is hydrogen.

Particularly preferred compounds of the invention include:

8-Chloro-2,4-dioxo-1-(3-methyl-1-butyl)-3-phenyloxycarbonylamino-5-phenyl-2,3,4,5-tetrahydro-1H-1,5-benzodiazepine;

7,8-Dichloro-3-[3-(N,N-dimethylamino)phenyloxycarbonylamino]-2,4-dioxo-1-(3-methylbut-1-yl)-5-phenyl-2,3,4,5-tetrahydro-1H-1,5-benzodiazepine;

8-Chloro-3-[3-(N,N-dimethylamino)phenyloxycarbonylamino]-2,4-dioxo-1-(3-methylbut-1-yl)-5-phenyl-2,3,4,5-tetrahydro-1H-1,5-benzodiazepine;

8-Chloro-2,4-dioxo-3-(3-methoxyphenyloxycarbonyl)amino-1-(3-methyl-1-butyl)-5-phenyl-2,3,4,5-tetrahydro-1H-1,5-benzodiazepine;

3-(3-Bromophenyloxycarbonyl)amino-8-chloro-2,4-dioxo-1-(3-methyl-1-1butyl)-5-phenyl-2,3,4,5-tetrahydro-1H-1,5-benzodiazepine;

1-(Adamantylmethyl)-2,4-dioxo-3-[3-(N,N dimethylamino)phenyloxycarbonylamino]-5-phenyl-2,3,4,5-tetrahydro-1H-1,5-benzodiazepine;

3-[3-(N,N-dimethylamino)phenyloxycarbonylamino]-2,4-dioxo-5-(2-fluorophenyl)-1-(3-methylbut-1-yl)-2,3,4,5-tetrahydro-1H-1,5-benzodiazepine;

2,4-Dioxo-1-(3-methylbut-1-yl)-5-phenyl-3-(phenyloxycarbonylamino)-2,3,4,5-tetrahydro-1H-1,5-benzodiazepine and the (+) enenatiomers thereof.

The pharmaceutically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

The compounds of formula (I) in which $R^7$ represents hydrogen may form pharmaceutically acceptable salts with suitable cations. Suitable pharmaceutically acceptable cations include alkali metal (e.g. sodium or potassium) and alkaline earth metal (e.g. calcium or magnesium) cations.

References hereinafter to a compound according to the invention includes both compounds of formula (I) and their pharmaceutically acceptable salts and solvates.

The compounds of the invention are potent and specific antagonists of gastrin and/or CCK. The compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

The compounds of the invention have also been shown to be antagonists of gastrin as demonstrated by their ability to inhibit pentagastrin-stimulated acid secretion from rat isolated gastric mueosa using the procedure described by J. J. Reeves and R. Stables in *Br. J. Pharmac.*, 1985, 86, p. 677–684.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol, (1985), 329, p36–41 and by V. L. Lucaites et al (1991) in J. Pharmacol. Exp. Ther., 256, 695–703.

The greater affinity of the compounds of the invention for the CCK-B receptor over the CCK-A receptor has also been established using the CCK receptor binding assays described by G Dal Fornos et al., *J. Pharmcol. Exp & Ther.* 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The compounds of the invention are also useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain rumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.01–2000 mg per day e.g. 0.01–500 mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable careers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending stabilising and/or dispersing agents. Alternatively the active ingredient may be in powder form which may be obtained by freeze drying for constitution with a suitable vehicle, e.g. sterile, pyrogen-free water, before use. The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R^1$–$R^{10}$ are as defined for the compounds of formula (I) unless otherwise stated.

According to a first general process (A) compounds of formula (I) may be prepared by reacting a compound of formula (II) wherein the groups $R^1$, $R^3$ and $R^{10}$ have the meanings defined above for formula (I).

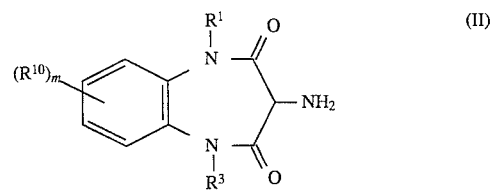

with the appropriate haloformate (III) $R^2OCOZ$, wherein Z is halogen e.g. chlorine or bromine and $R^2$ has the meanings defined above in formula (I). The reaction is preferably carded out in the presence of a base such as a tertiary amine, e.g. triethylamine or pyridine in a solvent such as a halohydrocabon e.g. dichloromethane and at a temperature within the range 0°–500°.

Compounds of formula (II) may be prepared by reduction of compounds of formula (III)

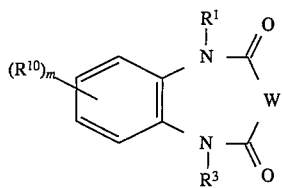   (III)

wherein W is CH—N₃ or C=N—NHPh.

Compounds of formula (III) wherein W is CH-N₃ may be reduced to a compound of formula (II) by hydrogenation in the presence of a suitable catalyst such as palladium, on a support such as carbon or calcium carbonate, or platinum (IV) oxide. The reaction conveniently takes place in the presence of a solvent such as an alkanol (e.g. ethanol) an ester (e.g. ethyl acetate) or acetic acid.

Compounds of formula (III) wherein W is C=N-NHPh may be reduced to a compound of formula (II) by reaction with zinc and acetic acid. This reaction may be carried out a temperature with the range 0°–500°.

Compounds of formula (III) wherein W is CHN₃ may be prepared from a compound of formula (II) wherein W is CH₂ by treatment with a strong base such as sodium hydride or potassium tert-butoxide followed by tri-isopropyl benzenesulphonyl azide. The reaction conveniently takes place in a solvent such as an ether (e.g. tetrahydrofuran) at a temperature in the range of −78° to 200°.

Compounds of formula (III) in which W is C=NNHPh may be prepared by reaction of the ortho-phenylenediamine (IV) with the diacid chloride (V), in a suitable solvent such as an ether e.g. tetrahydorfuran

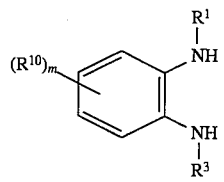   (IV)

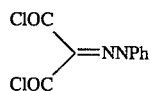   (V)

Compounds of formula (III) wherein W is CH₂ prepared by reaction of the corresponding compound (VI)

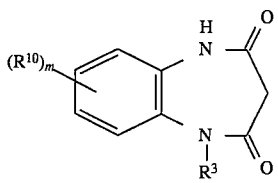   (VI)

with a compound R¹Y where Y is halogen (e.g. a chlorine or bromine atom) or a mesylate group under strongly basic conditions. Thus the reaction may conveniently be carried out by pretreating the compound of formula (VI) with a strong base such as sodium hydride in a suitable aprotic solvent such as an amide (e.g. N,N-dimethylformamide) at a temperature ranging from 0° to reflux.

In the above described reaction scheme when the group R¹ contains an hydroxyl group then this may be present in a protected form e.g. as an ether such as an arylmethyl ether e.g. a benzyl ether.

Compounds of formula (IV) are either known compounds or may be prepared by analogous methods. Thus for example a compound of formula (IV) may be prepared by alkylation of the amine (VII).

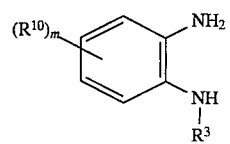   (VII)

Thus the amine (VII) may be reacted with the compound R¹Y, in which Y is chlorine or bromine, optionally in the presence of sodium iodide in a solvent such as N,N-dimethylformamide.

Compounds of formula (IV) wherein R¹ represents the group —CH₂—CH(OH)R¹$_a$ where R¹$_a$ is a C$_{1-4}$alkyl group may be prepared by reaction of compound (VII) with the epoxide (VIII) in a solvent such as an alkanol e.g. ethanol and in the presence of an acid catalyst such as p-toluene sulphonic acid.

   (VIII)

Compounds of formula (IV) where in R¹ is an optionally substituted alkyl group. May also be prepared from compound (VII) by reaction with a suitable aldehyde or ketone with concomitant or subsequent reduction of the reaction product. Thus for example a compound formula (IV) wherein R¹ is 2-(4-methylpentyl) may be prepared from compound (VII) by reaction with methylisobutyl ketone followed by reaction with sodium borohydride.

In general, the compounds of formula (III), (IV), (VI) and (VII) are either known compounds or may be prepared according to methods used for the preparation of known compounds, According to a further process (B) a compound of formula (I) may be converted into another compound of formula (I) using conventional techniques. Thus the compounds of formula (I) wherein R² is a phenyl group substituted by a carboxyl group may be prepared by hydrolysis of the corresponding compound of formula (I) wherein R² is phenyl substituted by alkoxycarbonyl.

In the processes described above the group R¹ and R² in the intermediates II, III, V and VI may be a group as defined in formula (I) or a group convertible thereto. Thus compounds of formula (I) wherein R¹ represents an alkyl group substituted by hydroxy may be prepared from the corresponding compounds of formula (I) when R¹ represents an acylalkyl group by reduction using a metal hydride such as sodium borohydride. The reaction is preferably carried out in an alkanol (e.g. methanol).

The foregoing series of reactions involve a number of alternative pathways which may start with the 1,5-benzodiazepine of formula (X) as defined above. Thus according to a further general process (C) a compound of formula (I) may be prepared by reacting a compound of formula (X) in one or more stages with reagents serving to introduce the groups R¹ and NHCOOR².

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as the use of chiral HPLC. Alternatively the required enantiomer may be prepared by the corresponding enantiomeric amine of formula (II) using any of the processes described above for preparing compounds of formula (I) from the amine (II). The enantiomers of the amine (II) may be prepared from the racemic amine (I) using conventional procedures such as salt formation with a suitably optically active acid.

The following examples, which are non-limiting, illustrate the invention.

In the Preparations and Examples, unless otherwise stated: Melting points (m.p.) were determined on a Buchi m.p. apparatus and are uncorrected. All temperatures refer to 0° C. Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield (☐) from $Me_4Si$ as an internal standard, and are assigned as singlets (s), doublets (d), doublet of doublets (dd) or multiplets (m). Column chromatography was carried out over silica gel (Merck AG Darmstadt, Germany). Solutions were dried over anhydrous sodium sulphate. "Petrol" refers to petroleum ether, b.p. 40°–60° C. Methylene chloride was redistilled over calcium hydride; tetrahydrofuran was redistilled over sodium; ethyl ether was redistilled over sodium and ethyl acetate was dried over activated molecular sieves. The following abbreviations are used in the text. EA=ethyl acetate, CH=cyclohexane, P=petroleum ether 40°–60° C., THF=tetrahydrofuran, DCM=dichloromethane, EE=ethyl ether. T.l.c. refers to thin layer chromatography on silica plates. All the compounds are intended as racemic mixtures unless otherwise indicated.

Intermediate 1

2,4-Dioxo-1-(3-methylbut-1-yl)-5-phenyl-2,3,4,5-tetrahydro-1H-1,5-benzodiazepine Sodium hydride 80% dispersion in oil (0.057 g) was added portionwise to a solution of 2,4-dioxo-5-phenyl-2,3,4,5-tetrahydro-1H-1,5-benzodiazepine (0.40 g) in dry dimethylformamide (15 ml). The reaction mixture was cooled to 0° and stirred for 30 min, then a solution of 3-methyl-1-bromobutane (0.23 ml) in dry dimethylformamide (4 ml) was added and stirring continued for 2 h. The reaction mixture was then diluted with water (100 ml), extracted with ethyl acetate (3×100 ml), washed with brine (2×50 ml), dried and concentrated in vacuo to give an oil which was purified by flash -chromatography (eluting with CH-EA 60:40) to give the title compound as a white solid (0.44 g). T.l.c. CH-EA (1:1), Rf=0.36.

Intermediate 2

3-Azido-2,4-Dioxo-1-(3-methylbut-1-yl)-5-phenyl-2,3,4,5-tetrahydro-1H-1,5-benzodiazepine A solution of the intermediate 1 (0.397 g) in THF (7 ml) was added to potassium ten-butoxide (0.154 g) in THF (6 ml) cooled to −78°. The reaction mixture was stirred for 30 min, then a cooled (−78°) solution of 2,4,6-triisopropylbenzenesulphonyl azide (0.49 g) in dry THF (7 ml) was added. After 5 min glacial acetic acid (0.07 ml) was added and the solution was allowed to warm to 23° and stirred for 24 h. The reaction mixture was diluted with ethyl acetate (40 ml) and washed with water (20 ml), saturated sodium hydrogen carbonate solution (20 ml) and brine (20 ml). The combined organic extracts were dried and concentrated in vacuo to give an oil (0.7 g). Purification by flash chromatography (eluting with CH-EA 60:40) gave the title compound as a white solid (0.25 g). T.l.c. CH-EA (60:40), Rf=0.3.

Intermediate 3

3-Amino-2,4-Dioxo-1-(3-methylbut-1-yl)-5-phenyl-2,3,4,5-tetrahydrol 1H-1,5-benzodiazepine 5% $Pd/CaCO_3$ (0.61 g) was added to a solution of the intermediate 2 (1.21 g) in ethyl acetate (60 ml) and ethanol (60 ml) and the reaction mixture was hydrogenated at 1 atm for 3.5 h. The catalyst was filtered off and the evaporated in vacuo to give the title compound as a pale yellow foam (1.14 g). T.l.c. DCM-methanol (95:5), Rf=0.55.

Intermediate 4

1-(3,3-Dimethylbut-1-yl)-2,4-dioxo-5-phenyl-2,3,4,5-tetrahydro-1H-1,5-benzodiazepine Sodium hydride 80% dispersion in oil (0.10 g) was added portionwise to a solution of 2,4-dioxo-5-phenyl-2,3,4,5-tetrahydro-1H-1,5-benzodiazepine (0.7 g) in dry dimethylformamide (60 ml). The reaction mixture was stirred for 30 min, then a solution of 3,3-dimethylbutylmethanesulphonate (0.575 g) in dry dimethylformamide (3 ml) was added. The reaction mixture was stirred at 90° for 50 min at 23° for 15 h, at 90° for 2h and at 140° for 45 min, then concentrated in vacuo. The residue was diluted with water (30 ml) and brine (20 ml) and extracted with ethyl acetate (150 ml); the organic layer was washed with water (2×50 ml) and brine (50 ml), dried and concentrated in vacuo. The crude product was purified by flash chromatography (eluting with CH-EA 1:1) to give the title compound as a white foam (0.4 g). T.l.c. CH-EA (1:1), Rf=0.39.

Intermediate 5

3-Azido-1-(3,3-dimethylbutyl)-2,4-dioxo-5-phenyl-2,3,4,5-tetrahydro-1H-1,5-benzodiazepine A solution of potassium tert-butoxide (0.146 g) in THF (7 ml), cooled to −70°, was added dropwise to a solution of the intermediate 4 (0.4 g) in THF (15 ml), cooled to −70°, under a nitrogen atmosphere. The solution was stirred for 20 min at −70°, then a solution of 2,4,6-triisopropylbenzenesulphonyl azide (0.530 g) in THF (7 ml), previously cooled to −70° and acetic acid (0.139 ml) were added. The reaction mixture was allowed to stand at 23° and stirred for 18 hrs, ethyl acetate (75 ml) added and the solution washed with water (2×50 ml), brine (2×30 ml), dried and concentrated in vacuo. The crude product was purified by flash chromatography (eluting with CH-EA 30:70) to give the title compound as a white foam (0.338 g). T.l.c. CH-EA (1:1), Rf=0.73.

Intermediate 6

3-Amino-1-(3,3-dimethylbutyl)-2,4-dioxo-5-phenyl-2,3,4,5-tetrahydro-1H-1,5-benzodiazepine A solution of the intermediate 5 (0.298 g) in a mixture of ethanol (18 ml) and ethyl acetate (7 ml) was stirred under hydrogen, at 1 atm., in presence of 5%$Pd/CaCO_3$ (0.186 g), at 23°, for 1.5 h, then more 5% $Pd/CaCO_3$ (0.180 g) was added and the reaction stirred for 1 h. The catalyst was filtered off on a pad of celite, washed with ethanol (20 ml) and the organic layer was concentrated in vacuo. The crude product was purified by flash chromatography (eluting with DCM-methanol 90:10) to give the title compound as a white foam (0.205 g). T.l.c. DCM-methanol (90:10), Rf=0.46.

Intermediate 7

2,4-Dioxo-5-phenyl-1-(3-methyl-2-oxo)butyl-2,3,4,5-tetrahydro-1H-1,5-benzodiazepine Sodium hydride 80% dispersion in oil (0.4 g) was added portionwise to a solution of 2,4-dioxo-5-phenyl-2,3,4,5-tetrahydro-1H-1,5-benzodiazepine (2 g) in dry dimethylformamide (50 ml), previously cooled to 0°. The reaction was stirred for 15 min at 0°, then a solution of 1-bromo-3-methyl-2-oxobutane (2.6 g) in dimethylformamide (10 ml) was added dropwise. The mixture was stirred at 0° for 45 min, ethyl acetate (450 ml) added and the solution washed with brine (4×100 ml), dried and concentrated in vacuo. The crude product was purified by flash chromatography (eluting with CH-EA 1:1) to give the title compound as a white foam (2.3 g). T.l.c. CH-EA (1:1), Rf=0.19.

Intermediate 8

3-Azido-2,4-dioxo-1-(3-methyl-2-oxo)butyl-5-phenyl-2,3,4,5-tetrahydro-1H-1,5-benzodiazepine A solution of potassium tert-butoxide (0.185 g) in THF (10 ml) was added dropwise to a solution of the intermediate 7 (0.5 g) in THF (20 ml), cooled to −70°, under a nitrogen atmosphere. The mixture was stirred for 20 min at −70°, then a solution of 2,4,6-triisopropylbenzenesulphonyl azide (0.688 g) in THF (10 ml), previously cooled to −70° and acetic acid (0.2 ml) were added. The reaction mixture was allowed to stand at 23° and stirred for 15 h, ethyl acetate (400 ml) added and the solution washed with brine (3×100 ml), dried and concentrated in vacuo. The crude product was purified by flash chromatography (eluting with CH-EA 1:1) to give the title compound as a foam. T.l.c. CH-EA (1:1), Rf=0.51.

Intermediate 9

3-Amino-2,4-dioxo-1-(3-methyl-2-oxo)butyl-5-phenyl-2,3,4,5-tetrahydro-1H-1,5-benzodiazepine A solution of the intermediate 8 (0.85 g) in ethanol (35 ml) was stirred under hydrogen, at 1 atm., in presence of 5% Pd/CaCO$_3$ (1 g), at 23°, for 2 h. The catalyst was filtered off on a pad of celite, washing with ethanol (30 ml) and the organic layer was concentrated in vacuo. The crude product was purified by flash chromatography (eluting with DCM-methanol 90:10) to give the title compound as a white foam (0.5 g). T.l.c. DCM-ethanol (95:5), Rf=0.56.

Intermediate 10

3-(N,N-dimethylamino)phenyl chloroformate)

A solution of 3-(N,N-dimethylamino)phenol (1.0 g) in dichloromethane (20 ml) was added, dropwise, to a solution of phosgene in toluene (1.93M, 30 ml) previously cooled to −5°. The resulting mixture was stirred at a temperature between −5 to 0° to 30', then decanted and concentrated in vacuo to a brown oil (0.63 g). IR: 1784 (C=O), 1616 and 1572 (C=C) cm-1; 1H-NMR: 7.23 (m); 6.65 (dd); 6.53 (dd); 6.50 (m); 2.96 (s).

Intermediate 11

2-(Adamant-2-yl)amino-diphenylamine

Sodium borohydride (1.873 g) was added portionwise to a mixture of 2-aminodiphenylamine (0.61 g), sodium acetate trihydrate (1.36 g) and 2-adamantanone (0.5 g) in acetic acid (2.1 ml), water (8 ml) and ethanol (6.5 ml) cooled to 0°. The reaction mixture was stirred at 23° for 1 hr, diluted with ethyl acetate (100 ml). The organic layer was washed with water (30 ml), a 10% solution of sodium hydroxide (2×25 ml), water (30 ml) and brine (20 ml), dried and concentrated in vacuo to yield a residue still containing the unreacted 2-adamantanone, which was removed by filtration. The filtrate was concentrated in vacuo and purified by flash chromatography (eluting with CH-EA 95:5) to give the title compound as a yellow solid (0.185 g). T.l.c. CH-EA (90:10), Rf =0.73.

Intermediate 12

1-(Adamant-2-yl)-2,4-dioxo-5-phenyl-3-phenylhydrazono-2,3,4,5-tetrahydro-1H-1,5-benzodiazepine The intermediate 11 (0.96 g) and 2-phenylhydrazonomalonyldichloride (0.89 g) were each taken up in THF (10 ml) and dropped in a flask containing THF (50 ml) maintained at 0° under a nitrogen atmosphere. After complete addition the solution was allowed to warm to room temperature and then heated to 50° for 3 h. The reaction mixture was concentrated in vacuo to give an oil, which was purified by flash chromatography (eluting with CH-EA 90:10) to give the title compound as a yellow solid (0.758 g). T.l.c. CH-EA (80:20), Rf 0.60.

Intermediate 13

1-(Adamant-2-yl)-3-amino-2,4-dioxo-5-phenyl-2,3,4,5-tetrahydro-1H-1,5-benzodiazepine A suspension of the intermediate 12 (0.745 g) in glacial acetic acid (10 ml) was added to a mixture of zinc dust (0.956 ) in glacial acetic acid (8 ml), cooled to 0°. The mixture was stirred at 23° for 3 h, then diluted with water (100 ml) and decanted from zinc. Solid sodium carbonate was added until pH=9 and the mixture extracted with ethyl acetate (3×100 ml). The combined organic extracts were dried and concentrated in vacuo to an oil which was ethyl acetate (50 ml), washed with a 10% solution of sodium hydroxide (60 ml), brine (2×60 ml), dried and concentrated in vacuo. The residue was triturated with ethyl acetate to give the title compound as a white solid (0.51 g). M.p. 231°–3° (dec). T.l.c. DCM-methanol (90:10), Rf 0.61.

Intermediate 14

2-Fluoro-2'-(3-methylbut-1-yl)amino-diphenylamine

1-Bromo 3-methylbutane (4.33 ml) was added to a solution of 2-amino-2'-fluorodiphenylamine (7.0 g) and sodium iodide (5.24 g) in dimethylformamide (250 ml) under a nitrogen atmosphere. The solution was stirred at 120° for 8 h, then cooled to room temperature, diluted with water (300 ml) and extracted with diethyl ether (2×250 ml). The combined organic extracts were washed with brine (300 ml), dried and concentrated in vacuo to an oil, which was purified by flash chromatography (eluting with CH-EA 95:5) to give the title compound as a yellow oil (6.3 g). T.l.c. CH-EA (9:1), Rf 0.75.

Intermediate 15

2,4-Dioxo-5-(2-fluorophenyl)-1-(3-methylbut-1-yl)-3-phenylhydraono-2,3,4,5-tetrahydro-1H-1,5-benzodiazepine The intermediate 14 (6.3 g) and 2-phenylhydrazonomalonyldichloride (6.8 g) were each taken up in THF (150 ml) and dropped in a flask containing THF (200 ml) maintained at −5° under a nitrogen atmosphere. After complete addition the solution was allowed to warm to room temperature and then heated to 50° for 2 h. The solution was concentrated in vacuo to an oil, which was purified by flash chromatography (eluting with CH-EA 8:2) to give the title compound as a yellow solid (5.8 g). M.p. 104°–105° T.l.c. CH-EA (7:3), Rf 0.59.

Intermediate 16

3-Amino-2,4-dioxo-5-(2-fluorophenyl)-1-(3-methylbut-1-yl)-2,3,4,5-tetrahydro-1H-1,5-benzodiazepine A solution of the intermediate 15 (5.8 g) in glacial acetic acid (50 ml) was added, dropwise, to a suspension of zinc dust (6.37 g) in glacial acetic acid (20 ml) cooled to 0°. The mixture was stirred at 23° for 3 h, then diluted with water (200 ml) and decanted from the zinc. Solid sodium carbonate was added until pH-9 and the mixture extracted with ethyl acetate (2×300 ml). The combined organic extracts were washed with brine (300 ml), dried and concentrated in vacuo to an oil which was purified by flash chromatography (eluting in gradient from CH-EA 2:1 to EA) to give the title compound as a white foam (2.8 g). M.p. 125°–60° T.l.c. DCM-methanol (30:1), Rf 0.38.

Intermediate 17

2-(3,3-Dimethylbut-1-yl)amino-2'-fluoro-diphenylamine

Sodium borohydride (22.7 g) was added portionwise to a mixture of 2-amino-2'-fluorodiphenylamine (8.0 g), sodium acetate trihydrate (16.33 g) and 3,3-dimethylbutyraldehyde (5 ml) in acetic acid (12.8 ml), water (50 ml) and ethanol (40 ml) cooled to 0° C. The solution was stirred at 23° for 30 min., then diluted with ethyl acetate (300 ml). The organic layer was washed with a 10% solution of sodium hydroxide (3×200 ml) and brine (200 ml), dried and concentrated in vacuo to an oil, which was purified by flash chromatography (eluting with CH-EA 9:1) to give the title compound as a yellow oil (7.44 g). T.l.c. CH-EA (9:1), Rf 0.85.

Intermediate 18

1-(3,3-Dimethylbut-1-yl)-2,4-dioxo-5-(2-fluorophenyl)-3-phenylhydrazono-2,3,4,5-tetrahydro-1H-1,5-benzodiazepine The intermediate 17 (7.738) and the 2-phenylhydrazonomalonyldichloride (7.978) were each taken up in THF (100 ml) and dropped in a flask containing THF (300 ml) maintained at −5° under a nitrogen atmosphere. After complete addition the solution was allowed to warm to room temperature and then heated to 50° for 3 h. The solution was concentrated in vacuo to an oil, which was purified by flash chromatography (eluting with CH-EA 8:2) to give the title compound as yellow solid (10.8 g). M.p. 112°–114°. T.l.c. CH-EA (8:2) Rf 0.40.

Intermediate 19

3-Amino-1-(3,3-dimethylbut-1-yl)-2,4-dioxo-5-(2-fluorophenyl)-2,3,4,5-tetrahydro-1H-1,5-benzodiazepine A solution of the intermediate 18 (10.1 g) in glacial acetic acid (80 ml) was added, dropwise, to a suspension of zinc dust (10.8 g) in glacial acetic acid (20 ml) cooled to 0°. The mixture was stirred at 23° for 2 h, then diluted with water (200 ml) and decanted from zinc. Solid sodium carbonate was added until pH-9 and the solution then extracted with ethyl acetate (3×250 ml). The combined organic extracts were washed with brine (400 ml), dried and concentrated in vacuo to an oil, which was purified by flash chromatography (eluting in gradient from CH-EA 2:1 to ethyl acetate) to give the title compound as a white foam (5.4 g). M.p. 98°–100°. T.l.c. DCM-methanol (20:0.5), Rf 0.3.

Intermediate 20

Methyl 2-(2-Adamantylethyl)mesylate

Triethylamine (0.26 ml) and mesylchloride (0.145 ml) were added to a solution of the 2-(2-adamantyl)ethanol (0.22 g) in dry dichloromethane (10 ml) under a nitrogen atmosphere. The resulting solution was stirred at 23° for 1 h, then washed with a saturated ammonium chloride solution (20 ml). The organic layer was dried, filtered and concentrated in vacuo to give the title compound as a colourless oil (0.28 g). T.l.c. CH-EA (7:3) Rf 0.7.

Intermediate 21

2-(2-Adamantylethyl)amino-diphenylamine

Sodium iodide (1.12 g) was added to a solution of 2-aminodiphenylamine (1.36 g) and intermediate 20 (1.92 g) in dimethylformamide (130 ml) under a nitrogen atmosphere. The reaction mixture was heated at 120° for 4 h; then the solution was cooled at 23°, diluted with water (120 ml) and extracted with ethyl acetate (5×30 ml). The organic layer was washed with water (2×30 ml) dried and concentrated in vacuo to yield a brown oil (2.1 g) which was purified by flash chromatography (eluting with CH-EA 98:2 to give the title compound as a yellow oil (0.92 g). T.l.c. CH-EA (98:2), Rf 0.35.

Intermediate 22

1-(2-Adamantylethyl)2,4-dioxo-5-phenyl-3-phenylhydrazono-2,3,4,5-tetrahydro-1H-1,5-benzodiazepine 2-phenylhydrazonomalonyldichloride (0.740 g) was taken up in THF (25 ml) and dropped in a flask containing the intermediate 21 in THF (25 ml) at 23°. After complete addition the solution was heated to 50° for 2 h, then cooled to 23° and concentrated in vacuo to give an oil (1.558 g) which was purified by flash chromatography (eluting with CH-EA 80:20) to give the title compound as a yellow solid (0.754 g). T.l.c. CH-EA (80:20), Rf=0.40. M.p. 130°–1°.

Intermediate 23

1-(2-Adamantylethyl)amino-2,4-dioxo-5-phenyl-2,3,4,5-tetrahydro-1H-1,5-benzodiazepine In a suspension of the intermediate 22 (0.734 g) in glacial acetic acid (10 ml) a mixture of zinc dust (0.694) in glacial acetic acid (8 ml) was added. The mixture was stirred at 23° for 2 h and decanted from zinc. 10% sodium carbonate solution was added until pH=9 and the mixture extracted with ethyl acetate (4×25 ml). The combined organic extracts were washed with brine (2×40 ml), dried and concentrated in vacuo. The residue (0.644 g) was purified by flash chromatography (eluting with EA:MeOH 95:5) to give the title compound (0.366 g). M.p. 196°–7°C T.l.c. EA-methanol (95:5), Rf=0.40.

Intermediate 24

4,5-Dichloro-2-nitrodiphenylamine

A mixture of 4,5-dichloro-2-nitroaniline (5.0 g), bromobenzene (16 ml) potassium carbonate (1.17 g) and copper(I) iodide (0.46 g) was heated to 150° for 36 h. The reaction mixture was concentrated in vacuo to give the crude compound which was purified by flash chromatography (eluting with CH-EA 90:10) to give the title compound (4.34 g) T.l.c. CH-EA (1:1), Rf 0.7.

Intermediate 25

2-Amino-4,5-dichloro-diphenylamine

Potassium carbonate (13.8 g) and sodium hydrosulfite (12.1 g) were added portionwise over 3 hour to a suspension of 4,5-dichloro-2-nitrodiphenylamine (4.34 g) in 95% ethanol (100 ml) and water (100 ml). The mixture was stirred at 23° for 20 h. The reaction mixture was then acidified to pH=4 with conc. hydrochloric acid (20 ml), then 10% solution of sodium hydroxide (80 ml) was added until pH=10 and the solution extracted with ethyl acetate (3>120 ml). The combined organic extracts were washed with brine (2×100 ml), dried and concentrated in vacuo to give the crude compound which was purified by flash chromatography (eluting with CH-EA 90:10 then 80:20) to give the title compound as a yellow foam (2.15 g). T.l.c. CH-EA (1:1), Rf 0.54.

Intermediate 26

4,5-Dichloro-2-(3-methylbut-1-yl)amino-diphenylamine

1-Bromo-3-methylbutane (1.2 ml) was added to a solution of the intermediate 25 (2.15 g) and sodium iodide (1.3 g) in dimethylformamide (70 ml) under a nitrogen atmosphere. The solution was stirred at 120° for 9 h, and at 23° C. for 20 h. A further amount of bromo-3-methylbutane (0.5 ml) was then added and stirring was continued at 120° for 8 h. The reaction mixture was diluted with ethyl acetate (300 ml) and washed with brine (150 ml). The combined organic extracts were dried and concentrated in vacuo to give an oil, which was purified by flash chromatography (eluting with CH-EA 95:5) to give the title compound as a yellow oil (1.72 g). T.l.c. CH-EA (1:1), Rf 0.70.

Intermediate 27

7-8-dichloro-2,4-Dioxo-1-(3-methylbut-1-yl)-5-phenyl-3-phenylhydrazone-2,3,4,5-tetrahydro-1H-1,5-benzodiazepine The intermediate 26 (1.72 g) and the 2-phenylhydrazonomalonyldichloride (1.53 g) were each taken up in THF (15 ml) and dropped in a flask containing THF (40 ml) maintained at 0° under a nitrogen atmosphere. After complete addition the solution was allowed to warm at 23° C., stirred for 45 min., then heated at 60° for 1 h and 30 min. The solution was diluted with ethyl acetate (150 ml), washed with brine (2×100 ml), dried and concentrated in vacuo to give an oil, which was purified by flash chromatography (eluting with CH-EA 95:5, increasing polarity to 80:20) to give the title compound as a yellow solid (1.85 g). T.l.c. CH-EA (1:1), Rf 0.66.

Intermediate 28

3-Amino-7-8-dichloro-2,4-dioxo-1-(3-methylbut-1-yl)-5-phenyl-2,3,4,5-tetrahydro-1H-1,5-benzodiazepine To the solution of the intermediate 27 (1 0 g) in glacial acetic acid (15 ml) at 0°, zinc dust (0.65 g) was added portionwise. The mixture was stirred at 23° for 6 h, then decanted from zinc, washed with ethyl acetate (150 ml) and then with 10% sodium hydroxide (150 ml) and brine (100 ml). The combined organic extracts were dried and concentrated in vacuo to give an oil which was purified by flash chromatography (eluting in gradient from CH-EA 1:1 to EA-methanol 80:20) to give the title compound (0.44 g). T.l.c. EA-methanol (27:3), Rf 0.59.

Intermediate 29

4-Fluoro-N'-(3-methylbut-1-yl)-N"-phenyl-1,2-benzendiamine

Bromo 3-methylbutane (0.38 ml) was added to a solution of the 5-fluoro N'-phenyl-1,2-benzendiamine (0.645 g) and sodium iodide (0.476 g) in dimethylformamide (25 ml) under a nitrogen atmosphere. The solution was stirred at 120° for 10 h, then cooled to room temperature, diluted with water (30 ml) and extracted with ethyl ether (2×25 ml). The combined organic extracts were washed with brine (30 ml), dried and concentrated in vacuo to give a red oil, which was purified by flash chromatography (eluting with CH-EA 9:1) to give the title compound as a brown oil (0.467 g). T.l.c. CH-EA (2:1), Rf 0.78.

Intermediate 30

2,4-Dioxo-7-fluoro-1-(3-methylbut-1-yl)-5-phenyl-3-phenylhydrazono-2,3,4,5-tetrahydro-1H-1,5-benzodiazepine The intermediate 29 (0.454 g) and the phenylhydrazonomalonyldichloride (0.49 g) were each taken up in THF (15 ml) and dropped in a flask containing THF (15 ml) maintained under a nitrogen atmosphere. After complete addition the solution was heated to 70° for 1 h. The solution was diluted with EA (20 ml), washed with 5% sodium hydrogen carbonate solution (20 ml) and brine (20 ml), dried and concentrated in vacuo to an oil, which was purified by flash chromatography (eluting with CH-EA 8:2) to give the title compound as a yellow foam (0.565 g). T.l.c. CH-EA (4:1), Rf 0.33.

Intermediate 31

3-Amino-2,4-dioxo-7-fluoro-1-(3-methylbut-1-yl)-5-phenyl-2,3,4,5-tetrahydro-1H-1,5-benzodiazepine Zinc dust (0.822 g) was added to a solution of the intermediate 30 (0.559 g) in glacial acetic acid (20 ml). The mixture was stirred at 23° for 2 h, then diluted with 10% solution of sodium hydroxide until pH=9 and the mixture extracted with ethyl acetate (2×30 ml). The combined organic extracts were washed with brine (30 ml), dried and concentrated in vacuo to give a brown oil (0.529 g) which was purified by flash chromatography (eluting with CH-Methanol 19/1 to give the title compound as a yellow foam (0.323 g). M.p. 125°–6° C. T.l.c. EA-methanol (19:1), Rf 0.45.

Intermediate 32

2-(2-Cyclopentyl-ethyl)-amino-2'-fluoro-diphenylamine

Sodium borohydride (17.86 g) was added portionwise to a mixture of 2-amino-2'-fluoro-diphenylamine (6.47 g), sodium acetate trihydrate (4.24 g) and cyclopentylacetaldehyde (3.58 g) in acetic acid (19.6 ml), water (76 ml) and ethanol (60 ml) cooled to 0°. The reaction mixture was stirred at 23° for 1 h and 30 min., then diluted with ethyl acetate (200 ml). The organic layer was washed with water (70 ml), a 10% solution of sodium hydroxide (70 ml), and brine (50 ml), dried and concentrated in vacuo to yield a residue which was purified by flash chromatography (eluting with CH-EA 9:1) to give the title compound as a yellow oil (3.35 g). T.l.c. CH-EA (9:1), Rf 0.78

Intermediate 33

1-(2-Cyclopentyl-ethyl)-2,4-dioxo-5-(2-fluorophenyl)-3-phenylhydrazono-2,3,4,5-tetrahydro-1H-1,5-benzodiazepine The intermediate 32 (3.30 g) and 2-phenylhydrazonomalonyldichloride (3.25 g) were each taken up in THF (25 ml) and dropped in a flask containing THF (150 ml) maintained at 0° under a nitrogen atmosphere. After complete addition the solution was allowed to warm to 23° C.; the reaction mixture was then heated to 55° for 3 h and concentrated in vacuo. The residue was taken up in cyclohexane/EA 7/3 (40 ml); the precipitate was filtered off and washed with cyclohexane to give the title compound as a yellow solid (3.75 g). T.l.c. CH-EA (1:1), Rf 0.71.

Intermediate 34

3-Amino-1-(2-cyclopentyl-ethyl)-2,4-dioxo-5-(2-fluoro)phenyl-2,3,4,5-tetrahydro-1H-1,5-benzodiazepine To a suspension of Zinc dust (4.70 g) cooled to 0°, intermediate 33 (3.70 g) in glacial acetic acid (50 ml) was added. The mixture was stirred at 23° for 5 h, then, diluted with water (250 ml) and decanted from the zinc. Solid sodium carbonate was added until Ph 9, then EA (300 ml) was added and the organic extracts were dried and concentrated in vacuo to give a residue which was purified by flash chromatography (eluting with CH-EA 1:1) then with DCM/methanol 9:1 to give the title compound (2.55 g) as a white foam. T.l.c. DCM-methanol (90:10), Rf 0.63.

Intermediate 35

2-(Bicyclo[2.2.1]-5-heptene-2-yl-methyl)-amino-diphenylamine

To a solution of 2-aminodiphenylamine (3.06 g) in toluene (100 ml) 5-norbornene-2-carboxaldehyde (2 ml) was added and the mixture was refluxed under a nitrogen atmosphere, in the presence of 4A molecular sieves, for 6 hrs. The solution was decanted from the sieves and the solvent was evaporated. The residue was dissolved in methanol (100 ml) and sodium borohydride (5.70 g) was added portionwise. The mixture was stirred at 23° for 12 hr., diluted with ethyl acetate (100 ml), washed with a 10% potassium carbonate solution (2×100 ml) and brine (100 ml), then dried and concentrated in vacuo. The crude material was purified by flash chromatography (eluting with CH-EA 95:5) to give the title compound (0.92 g) as a yellow glass. T.l.c. CH-EA (95:5), $R_f$ 0.56.

Intermediate 36

1-(Bicyclo[2.2.1]-5-heptene-2-ylmethyl)-2,4-dioxo-5-phenyl-3-phenylhydrazono-2,3,4,5-tetrahydro-1H-1,5-benzodiazepine Intermediate 35 (0.85 g) and 2-phenylhydrazonomalonyldichloride (0.87 g) were each taken up in dry THF (40 ml) and dropped into a flask containing THF (10 ml). The mixture was refluxed, under nitrogen, for 2 hrs, then it was diluted with ethyl acetate (50 ml) and washed with a 5% sodium bicarbonate solution (50 ml) and brine (50 ml). The organic layer was dried, concentrated in vacuo and purified by flash chromatography (eluting with CH-EA 9:1) to give the title compound (1.27 g) as a yellow foam. M.p. 149°–151°. T.l.c. (CH-EA 8:2) Rf 0.34.

Intermediate 37

3-Amino-1-(Bicyclo[2.2.1]-5-heptene-2-yl-methyl)-2,4-dioxo-5-phenyl-2,3,4,5-tetrahydro-1H-1,5-benzodiazepine Zinc dust (1.5 g) was added to a solution of the intermediate 36 (0.49 g) in glacial acetic acid (20 ml). The mixture was stirred at 23° for 12 hrs, then it was filtered through a pad of celite. The filtrate was concentrated in vacuo; the residue was taken up in ethyl acetate (70 ml) and washed with a 10% sodium hydroxide solution (2×50 ml) and brine (2×50 ml), then dried and concentrated in vacuo. Purification by flash chromatography (eluting with EA-MeOH 9:1) afforded the title compound (0.26 g) as a light yellow foam. T.l.c. (EA-MeOH 9:1), $R_f$ 0.37.

Intermediate 38

3-Amino-1-(bicyclo[2.2.1]-2-heptylmethyl)-2,4-dioxo-5-phenyl-2,3,4,5-tetrahydro-1H-1,5-benzodiazepine The intermediate 36 (0.506 g), suspended in methanol (20 ml), was hydrogenated at 1 atmosphere, in the presence of 5% Pd/C (0.271 g) and concentrated hydrochloric acid (1.6 ml), for 7 h. Then, the mixture was filtered through a pad of celite and the solvents were evaporated. The residue was taken up in ethyl acetate (100 ml) and washed with a 5% sodium hydroxide solution (2×100 ml) and brine (100 ml); the organic layer was dried, concentrated in vacuo and purified by flash chromatography (eluting with EA-MeOH

Intermediate 39

2-[Bicyclo[2.2.1]-2-heptyl]amino-diphenylamine

A mixture of 2-aminodiphenylamine (5.0 g), 2-norbornanone (3.0 g) and molecular sieves in dry toluene (200 ml) was heated to 120° for 6 h. The mixture was allowed to cool to room temperature, filtered and the solution concentrated in vacuo. The residue was dissolved in ethanol (200 ml), then sodium borohydride (3.0 g) was added portionwise. The resulting mixture was stirred at 23° for 30 min, diluted with water (150 ml) and extracted with ethyl acetate (300 ml). The organic layer was washed with brine (2×200 ml), dried and concentrated in vacuo to an oil which was purified by flash chromatography (eluting with CH-EA 9:1) to give the title compound as a yellow oil (3.5 g). T.l.c. CH-EA (9:1), Rf 0.74.

Intermediate 40

1-[Bicyclo[2.2.1]-2-heptyl]-2,4-dioxo-5-phenyl-3-phenylhydrazono-2,3,4,5-tetrahydro-1H-1,5-benzodiazepine

The intermediate 39 (3.77 g) and the 2-phenylhydrazonomalonyldichloride (3.98 g) were each taken up in THF (70 ml) and dropped into a flask containing THF (60 ml) under a nitrogen atmosphere. After complete addition the solution was heated to 50° for 1 h. The solution was concentrated in vacuo to an oil which was purified by flash chromatography (eluting with CH-EA 8:2) to give the title compound as a yellow solid (6.0 g). M.p. 110°–111° T.l.c. CH-EA (7:3), Rf 0.72 and 0.66.

Intermediate 41

3-Amino-1-[bicyclo[2.2.1]-2-heptyl]-2,4-dioxo-5-phenyl-2,3,4,5-tetrahydro-1H-1,5-benzodiazepine

Zinc dust (3.26 g) was added to a solution of the intermediate 40 (3.0 g) in glacial acetic acid (30 ml). The mixture was stirred at 23° for 4 h, then decanted from zinc. The solution was basified until pH=9 using 10% sodium hydroxide solution and extracted with ethyl acetate (2×100 ml). The combined organic extracts were washed with brine (150 ml), dried and concentrated in vacuo to a residue which was triturated with diethyl ether to give the title compound as a white solid (1.34 g). M.p. 172°–3°. T.l.c. EA-MeOH (95:5), Rf 0.3.

Intermediate 42

2-(2-Adamantylmethyl)amino-diphenylamine

A solution of sodium acetate trihydrate (6.45 g) and acetic acid (5 ml) in water was added to a mixture of 2-adamantanecarboxaldehyde (2.6 g) and 2-aminodiphenylamine (2.84 g) in ethanol (130 ml). Then sodium borohydride (5.97 g) was added portionwise. The resulting mixture was stirred at 23° for 6 h, then diluted with water (80 ml) and extracted with ethyl acetate (2×150 ml). The combined organic extracts were washed with brine (150 ml), dried and concentrated in vacuo to a residue, which was purified by flash chromatography to give the title compound as a yellow oil (2.15 g). T.l.c. CH-EA (8:2), Rf 0.86.

Intermediate 43

1-(2-Adamantylmethyl)-2,4-dioxo-5-phenyl-3-phenylhydrazono-2,3,4,5-tetrahydro-1H-1,5-benzodiazepine

A solution of 2-phenylhydrazonomalonyldichloride (1.78 g) in THF (50 ml) was added to solution of the intermediate 42 (2.0 g) in THF (50 ml) under a nitrogen atmosphere. The resulting solution was heated to 50° for 1 h., then concentrated in vacuo to a residue which was purified by flash chromatography (eluting with CH-EA 9:1) to give the title compound as a yellow solid (1.95 g). M.p. 135°–6° (dec) T.l.c. CH-EA (8:2), Rf=0.48.

Intermediate 44

1-(2-Adamantylmethyl)-3-amino-2,4-dioxo-5-phenyl-2,3,4,5-tetrahydro-1H-1,5-benzodiazepine

Zinc dust (1.84 g) was added to a solution of the intermediate 43 (1.9 g) in glacial acetic acid (20 ml). The mixture was stirred at 23° C. for 2 h, then decanted from zinc. The solution was basified until pH=9 using 10% sodium hydroxide solution and extracted with ethyl acetate (2×80 ml). The combined organic extracts were washed with brine (100 ml), dried and concentrated in vacuo to a residue which was purified by flash chromatography (eluting in gradient from CH-EA 1:1 to EA) to give the title compound as a yellow solid (0.95 g). M.p. 209°–210°. T.l.c. EA-MeOH (20:1), Rf 0.38.

Intermediate 45

1-(1-Adamantyl)methyl-2,4-dioxo-5-phenyl-2,3,4,5-tetrahydro-1H-1,5-benzodiazepine

Sodium hydride 80% dispersion in oil (0.07 g) was added portionwise to a solution of 2,4-dioxo-5-phenyl-2,3,4,5-tetrahydro-1H-1,5-benzodiazepine (0.5 g) in DMF (50 ml). The reaction mixture was stirred for 30 min, then a solution of 1-adamantylmethyl methanesulfonate (0.537 g) in DMF (3 ml) was added. The reaction mixture was stirred at 120° for 7 h and at 23° for 15 h, then concentrated. The residue was diluted with ethyl acetate (100 ml) washed with brine (2×30 ml) and water (50 ml), dried and concentrated "in vacuo". The crude product was purified by flash chromatography (eluting with CH-EA 1:1) to give the title compound as a white foam (0.15 g). T.l.c. CH-EA (1:1), $R_f$=0.42.

Intermediate 46

1-(1-Adamantyl)methyl-1-(2-phenylethyl)-3-azido-2,4-dioxo-5-phenyl-2,3,4,5-tetrahydro-1H-1,5-benzodiazepine

A solution of potassium tert-butoxide (0.146 g) in THF (7 ml) was added dropwise to a solution of the intermediate 45 (0.4 g) in THF (15 ml), cooled to −70°, under a nitrogen atmosphere. The mixture was stirred for 20 mm at −70°, then a solution of 2,4,6-triisopropylbenzenesulphonyl azide (0.53 g) in THF (7 ml), previously cooled to −70° and acetic acid (0.14 ml) were added. The reaction mixture was allowed to stand at 23° and stirred for 15 h, ethyl acetate (70 ml) was then added and the solution was washed with water (2×50 ml) and brine (2×30 ml), dried and concentrated "in vacuo". The crude product was purified by flash chromatography (eluting with CH-EA 70:30) to give the title compound as a white foam (0.338 g). T.l.c. CH-EA (1:1), $R_f$=0.73.

Intermediate 47

1-(1-Adamantyl)methyl-3-amino-2,4-dioxo-5-phenyl-2,3,4,5-tetrahydro-1H-1,5-benzodiazepine A solution of the intermediate 46 (0.18 g) in ethanol (10 ml) and ethyl acetate (8 ml) was stirred under hydrogen, at 1 atm., in presence of 5% Pd/CaCO$_3$ (0.2 g), at 23°, for 3 h, then the catalyst was filtered off on a pad of celite and the organic layer was concentrated "in vacuo". The crude product was purified by flash chromatography (eluting with DCM-methanol 90:10) to give the title compound as a white foam (0.15 g). T.l.c. DCM-methanol (90:10), R$_f$=0.51.

Intermediate 48

5-Fluoro N'-phenyl-1,2-benzendiamine

A solution of potassium carbonate (2.76 g) and sodium hydrosulfite (2.61 g) in water (80 ml) was added to a suspension of the 5-fluoro-2-nitro-N-phenylaniline (14.9 g) in 95% ethanol (120 ml). The mixture was stirred at 23° for 1 h, then a further amount of potassium carbonate (0.87 g) and sodium hydrosulfite (1.38 g) in water 40 ml) was added. The reaction mixture was acidified to pH=3.5 with conc. hydrochloric acid and concentrated in vacuo. A 10% solution of sodium hydroxide was added until pH=10 and the solution was extracted with ethyl acetate (200 ml). The combined organic extracts were washed with brine (200 ml), dried and concentrated in vacuo to give the crude compound which was purified by flash chromatography using CH-EA 2/1 as eluent to give the title compound as a brown solid (0.703 g). M.p. 83°–84°. T.l.c. CH-EA (2:1), Rf 0.45.

Intermediate 49

N'-(Adamantylmethyl)-4-Fluoro-N"-phenyl-1,2-benzendiamine

To a solution of 1-adamantanecarboxaldehyde (0.739 g) and intermediate 48 (0.501 g) in ethanol (30 ml) a buffer prepared with sodium acetate trihydrate (1.84 g) and glacial acetic acid (1.44 ml) in water (15 ml) was added and the mixture was stirred at 23°. A further amount of ethanol (15 ml) was added to get a clear solution and sodium borohydride (1.703 g) was added portionwise. After complete addition the mixture was stirred at 23° for 20, diluted with ethyl acetate (30 ml); the combined organic extracts were washed with potassium carbonate (30 ml), brine (30 ml), dried and concentrated in vacuo to give a brown oil (1.78 g) which was purified by flash chromatography (eluting with CH-EA 6:1 then 2:1) to give the title compound as an orange oil (0.466 g). T.l.c. CH-EA (2:1 ), Rf 0.44.

Intermediate 50

1-(Adamantylmethyl)-2,4-Dioxo-7-fluoro-5-phenyl-3-phenylhydrazono-2,3,4,5-tetrahydro-1H-1,5-benzodiazepine The intermediate 49 (0.460 g) and the phenylhydrazono-malonyldichloride (0.382 g) were each taken up in THF (15 ml) and dropped in a flask containing THF (15 ml) maintained under a nitrogen atmosphere. After complete addition the solution was heated to 70° for 1 h. The solution was diluted with EA (20 ml), washed with 5% sodium hydrogen carbonate solution (20 ml) and brine (20 ml), dried and concentrated in vacuo to a red foam (0.753 g), which was purified by flash chromatography (eluting with CH-EA 4:1) to give the title compound as a yellow foam (0.558 g). T.l.c. CH-EA (2:1 ), Rf0.61.

Intermediate 51

1-(Adamantylmethyl)-3-Amino-2,4-dioxo-7-fluoro-5-phenyl-2,3,4,5-tetrahydro-1H-1,5-benzodiazepine Zinc dust (0.694 g) was added to a solution of the intermediate 49 (0.555 g) in glacial acetic acid (20 ml). The mixture was stirred at 23° for 4 h, then a further amount of Zinc dust (0.350 g) was added and stirring was continued for 20 h. The reaction mixture was diluted with 10% solution of sodium hydroxide until pH=9 and the mixture extracted with DCM (2×30 ml). The combined organic extracts were washed with brine (30 ml), dried and concentrated in vacuo to give a brown foam (0.441 g) which was purified by flash chromatography (eluting with CH-Methanol 19/1) to give the title compound as a yellow foam (0.49 g). T.l.c. EA-methanol (19:1), Rf 0.49.

Intermediate 52

5-Fluoro-N-(4-Fluorophenyl)2-nitro aniline

A mixture of 2,4-difluoronitrobenzene (5.5 ml), 4-fluoro aniline (14.2 ml) and sodium carbonate (5.3 g) was heated at 180° for 3 h. The reaction mixture was cooled to room temperature, then diluted with DCM, washed with water (50 ml), brine (2×50 ml) dried and evaporated under vacuum to give the crude compound (22.6 g), which was purified by flash chromatography with CH-EA 4/1 to give the title compound as an orange solid (12.35 g). M.p. 115°–6° T.l.c. CH-EA (10:1), Rf 0.52.

Intermediate 53

4-Fluoro N'-[4-fluorophenyl]-1,2-benzendiamine

A solution of potassium carbonate (8.292 g) and sodium hydrosulfite (6.964 g) in water (200 ml) was added to a suspension of the intermediate 52 (2.502 g) in 95% ethanol (350 ml). The mixture was stirred at 23° for 1 h, the reaction mixture was acidified to pH=3.5 with conc. hydrochloric acid and concentrated in vacuo to half volume. A 10% solution of sodium hydroxide was added until pH=10 and the solution was extracted with ethyl acetate (200 ml). The combined organic extracts were washed with brine (200 ml), dried and concentrated in vacuo to give the crude compound (2.93 g) which was purified by flash chromatography using CH-EA 3/2 as eluent to give the title compound as a brown oil (1.64 g). M.p. 83°–84°. T.l.c. CH-EA (2:1), Rf 0.35.

Intermediate 54

N'-(Adamantylmethyl)-4-Fluoro-N"-(4-fluorophenyl)-1,2-benzendiamine

To a solution of 1-adamantanecarboxaldehyde (1.223 g) and intermediate 53 (1.64 g) in ethanol (50 ml) a buffer prepared with sodium acetate trihydrate (3.04 g) and glacial acetic acid (004 ml) in water (25 ml) was added and the mixture was stirred at 23°. A further amount of ethanol (15 ml) was added to get a clear solution and sodium borohydride (2.8 g) was added portionwise. The mixture was stirred at 23° for 20 h, and then diluted with ethyl acetate (30 ml). The combined organic extracts were washed with potassium carbonate (30 ml) with brine (30 ml), dried and concentrated in vacuo to give a red oil (3.102 g) which was purified by flash chromatography (eluting with CH-EA 15:1 to give the title compound as an orange oil (0.854 g). T.l.c. CH-EA (9:1), Rf 0.59.

Intermediate 55

1-(Adamantylmethyl)-2,4-Dioxo-7-fluoro-5-(4-fluorophenyl)-3-phenylhydrazono-2,3,4,5-tetrahydro-1H-1,5-benzodiazepine The intermediate 54 (0.850 g) and the phenylhydrazonomalonyldichloride (0.565 g) were each taken up in THF (30 ml) and dropped in a flask containing THF (30 ml) maintained under a nitrogen atmosphere. After complete addition the solution was heated to 70° C. for 3 h. The solution was diluted with EA (100 ml), washed with 5% sodium hydrogen carbonate solution (100 ml) and brine (100 ml), dried and concentrated in vacuo to a red foam (1.268 g), which was purified by flash chromatography (eluting with CH-EA 3:1) to give the title compound as a yellow foam (0.562 g). T.l.c. CH-EA (3:1), Rf 0.46.

Intermediate 56

1-(Adamantylmethyl)-3-Amino-2,4-dioxo-7-fluoro-5-(4-fluorophenyl)-2,3,4,5-tetrahydro-1H-1,5-benzodiazepine Zinc dust (0.673g) was added to a solution of the intermediate 55 (0.557 g) in glacial acetic acid (20 ml). The mixture was stirred at 23° C. for 6 h, filtered and evaporated to dryness; the residue was dissolved in water (80 ml), the solution was basified with solid sodium hydroxide until ph=9, extracted with EA (100 ml). The combined organic extracts were washed with brine (2×30 ml), dried and concentrated in vacuo to give a yellow foam (0.547 g) which was purified by flash chromatography (eluting with EAM-ethanol 9/1 to give the title compound as a white solid (0.322 g) M.p. 232°–3°. T.l.c. EA-methanol (9:1), Rf 0.56.

Intermediate 57

2-Amino-4-chlorodiphenylamine

Potassium carbonate (13 g) and sodium hydrosulphite (11.4 g) were added portionwise over 3 hour to a suspension of 4-chloro-2-nitrodiphenylamine (3.6 g) in 95% ethanol (100 ml) and water (100 ml). The mixture was stirred at 23° for 20 h. The reaction mixture was then acidified to pH=4 with conc. hydrochloric acid (20 ml); then 1.0% solution of sodium hydroxide (80 ml) was added until pH=10 and the solution extracted with ethyl acetate (2×150 ml). The combined organic extracts were washed with brine (2×150 ml), dried and concentrated in vacuo to give the crude compound as a yellow solid (7.8 g) which was purified by flash chromatography (eluting with CH-EA 90:10 then 70:30) to give the title compound as a yellow foam (2.37 g). T.l.c. CH-EA (1:1), Rf 0.66.

Intermediate 58

4-Chloro-2-(3-methylbut-1-yl)amino-diphenylamine

Bromo 3-methylbutane (0.62 ml) was added to a solution of the intermediate 57 (1.00 g) and sodium iodide (0.7 g) in dimethylformamide (40 ml) under a nitrogen atmosphere. The solution was stirred at 120° for 12 h, then cooled at 23° C., diluted with ethyl acetate (150 ml) and washed with brine (3×100 ml). The combined organic extracts were dried and concentrated in vacuo to give an oil, which was purified by flash chromatography (eluting with CH-EA 95:5) to give the title compound as a yellow oil (0.74 g). T.l.c. CH-EA (1:1), Rf 0.76.

Intermediate 59

8-Chloro-2,4-Dioxo-1-(3-methylbut-1-yl)-5-phenyl-3-phenylhydrazono-2,3,4,5-tetrahydro-1H-1,5-benzodiazepine The intermediate 58 (0.74 g) and the 2-phenylhydrazonomalonyldichloride (0.75 g) were each taken up in THF (15 ml) and dropped in a flask containing THF (20 ml) maintained at 0° under a nitrogen atmosphere. After complete addition, the solution was allowed to warm to 23° C., stirred for 30 min., then heated at 60° for 2 h. The solution was diluted with ethyl acetate (120 ml), washed with brine (2×100 ml), dried and concentrated in vacuo to give an oil, which was purified by flash chromatography (eluting with CH-EA 95:5, increasing polarity to 70:30) to give the title compound as a yellow solid (0.91 g). T.l.c. CH-EA (1:1), Rf 0.68.

Intermediate 60

3-Amino-8-chloro-2,4-dioxo-1-(3-methylbut-1-yl)-5-phenyl-2,3,4,5-tetrahydro-1H-1,5-benzodiazepine To the solution of intermediate 59 (0.9 g) in glacial acetic acid (20 ml) at 0°, zinc dust (1.14 g) was added portionwise. The mixture was stirred at 23° for 1 h, then decanted from zinc, washed with ethyl acetate (150 ml) and then with 10% sodium hydroxide (150 ml) and brine (100 ml). The combined organic extracts were dried and concentrated in vacuo to an oil which was purified by flash chromatography (eluting in gradient from CH-EA 1:1 to EA-methanol 27:3) to give the title compound (0.53 g). T.l.c. EA-methanol (27:3), Rf 0.6.

Intermediate 61

2,4-Dioxo-1-(3-methylbut-1-yl)-5-phenyl-2,3,4,5-tetrahydro-1H-1,5-benzodiazepine NaH 80% dispersion in oil (0.057 g) was added to a solution of 2,4-dioxo-5-phenyl-2,3,4,5-tetrahydro-1H-1,5-benzodiazepine (0.40 g) in dry DMF (15 ml). The reaction mixture was cooled at 0° and stirred for 15 min, 1-bromo-3-methyl-butane (0.23 ml) in dry DMF (4 ml) was added and stirring continued for 2 h. The reaction mixture was then diluted with water (100 ml), extracted with ethyl acetate (3×100 ml), washed with brine (2×50 ml), dried and concentrated in vacuo to give an oil (0.75 g) which was purified by flash chromatography (eluting with CH-EA 60:40) to give the title compound as a white solid (0.44 g). T.l.c. CH-EA (1:1), Rf. 0.36

Intermediate 62

3-Azido-2,4-Dioxo-1-(3-methylbut-1-yl)-5-phenyl-2,3,4,5-tetrahydro-1H-1,5-benzodiazepine A solution of the intermediate 61 (0.397 g) in dry THF (7 ml) was added to potassium tert-butoxide (0.154 g) in dry THF (6 ml) cooled at −78°. The reaction mixture was stirred for 30 mm, then a cooled (−78°) solution of 2,4,6-triisopropyl-bertzenesulphonylazide (0.49 g) in dry THF (7 ml) was added. After 5 min glacial acetic acid (0.07 ml) was added and the solution was allowed to warm at 23° and stirred for 24 h. The reaction mixture was diluted with ethyl acetate (40 ml) and washed with water (20 ml) saturated sodium hydrogen carbonate solution (20 ml) and brine (20 ml). The combined organic extracts were dried and concentrated in vacuo to give an oil (0.7 g). Purification by flash chromatography (eluting with CH-EA 60:40) gave the title compound as a white solid (0.25 g) T.l.c. CH-EA (60:40), Rf 0.3.

Intermediate 63

3-Amino-2,4-Dioxo-1-(3-metbylbut-1-yl)-5-phenyl-2,3,4,5-tetrahydro-1H-1,5-benzodiazepine 5% Pd/CaCO$_3$ (0.61 g) was added to a solution of intermediate 62 (1.21 g) in ethyl acetate (60 ml) and ethanol (60 ml) and the reaction mixture was hydrogenated at 1 atm for 3 h and 30 min. The catalyst was filtered off and the solvent evaporated in vacuo to give the title compound as a pale yellow foam (1.14 g). T.l.c. DCM-methanol (95:5), Rf 0.55.

Intermediate 64

3-Amino-2,4-Dioxo-1-(3-methylbut-1-yl)-5-phenyl-2,3,4,5-tetrahydro-1H-1,5-benzodiazepine (1S)-(+)-10-camphorsulphonic salt To intermediate 63 (2.05 g) dissolved in hot ethyl acetate (35 ml), (1S)-(+)-10-camphorsulphonic acid was added. The resulting salt (5b) was crystallized out from the cool solution by dropwise addition of cyclohexane; the precipitate was filtered off and washed with cold cyclohexane to give a (+)/(−) 3/97 mixture of diastereomeric salt (1.11 g) and mother liquors. Recrystallization (twice) from 2-propanol afforded the pure title compound (0.49 g). IR: 2750-2600 (NH$_3$), 1736, 1713, 1700 (C=O) cm$^{-1}$;

Intermediate 65

3-Amino-2,4-Dioxo-1-(3-methylbut-1-yl)-5phenyl-2,3,4,5-tetrahydro-1H-1,5-benzodiazepine (1R)-(−)-10-camphorsulphonic salt The mother liquors obtained after the initial precipitation of intermediate 64 were evaporated to dryness to give a solid (2.19 g). The residue was taken up in ethyl acetate (30 ml), extracted with a 5% ammonia solution (20 ml) and washed with brine (20 ml), the organic layer dried and evaporated in vacuo to give a residue (1.0 g). (1R)-(−)-10-camphorsulphonic acid in ethyl acetate (6 ml) was added to the solution of the residue (1 g) in ethyl acetate (5 ml) and the resulting solution was stirred at 0° for 2 h. The obtained precipitate was filtered off, washed with ethyl acetate (20 ml) and dried to give the title compound (0.97 g). 1H-NMR: 9.0-7.2 (m); 7.5 (d): 7.45-7.2 (m); 7.18 (t); 6.97 (d); 5.04 (s); 4.6 (m); 3.68 (m); 3.20 (m); 2.70 (m); 2.42 (m); 2.22 (m); 2.0-1.8 (m) 1.7-1.2 (m); 1.0-0.7 (m).

Intermediate 66

(+)-3-Amino-2,4-Dioxo-1-(3-methylbut-1-yl)-5-phenyl-2,3,4,5-tetrahydro-1H-1,5-benzodiazepine Intermediate 65 (0.95 g) was suspended in ethyl acetate (130 ml), washed with a 5% ammonia solution (70 ml) and stirred at 23° for 10 mm. The organic layer was separated, washed with brine (3×70 ml) dried and concentrated in vacuo to give the crude compound. Purification by flash chromatography (eluting with acetone-methanol 9:1) gave the title, compound as a white foam (0.51 g). IR: 3375 (NH$_2$), 1715-1661 (C=C), 1591 cm$^1$; 1H-NMR: 7.5-7.1 (m); 6.95 (dd); 4.6-4.5 (m), 4.24 (s); 3.8-3.65(m); 1.8(m); 1.62-1.4 (m); 0.92 (d); 0.89 (d).

Intermediate 67

1-(2,2-Dimethylethoxycarbonylmethyl)-2,4-dioxo-5-phenyl-2,3,4,5-tetrahydro-1H-1,5-benzodiazepine Sodium hydride 80% dispersion in oil (0.155 g) was added portionwise to a solution of 2,4-dioxo-5-phenyl-2,3,4,5-tetrahydro-1H-1,5-benzodiazepine (1.022 g) in DMF (30 ml) previously cooled to 0°. The reaction was stirred for 15 min at 23°, then t-butyl bromoacetate (0.7 ml) was added. The solution was stirred at 23° for 1 h, then brine (100 ml) was added and the mixture extracted with ethyl acetate (3×30 ml), dried and concentrated "in vacuo". The crude product was purified by flash chromatography (eluting with CH-EA 60:40) to give the title compound as a white powder (1.31 g). T.l.c. CH-EA (60:40), R$_f$=0.4.

Intermediate 68

3-Azido-1-(2,2-dimethylethoxycarbonylmethyl)-2,4-dioxo-5-phenyl-2,3,4,5-tetrahydro-1H-1,5-benzodiazepine A solution of the intermediate 67 (0.5 g) in THF (6 ml), cooled to −70°, was added dropwise to a solution of potassium tert-butoxide (0.168 g) in THF (6 ml) cooled to −70°, under a nitrogen atmosphere. The reaction mixture was stirred for 30 mm at −70°, then a solution of 2,4,6-triisopropylbenzenesulphonyl azide (0.556 g) in THF (6 ml), previously cooled to −70° and acetic acid (0.078 ml) were added. The reaction mixture was allowed to stand at 23° and stirred for 18 h, ethyl acetate (30 ml) was added and the solution was washed with brine (3×100 ml), a saturated solution of sodium hydrogen carbonate (20 ml), brine (20 ml), dried and concentrated "in vacuo". The crude product was purified by flash chromatography (eluting with CH-EA 70:30) to give the title compound as a white foam (0.5 g). T.l.c. CH-EA (1:1), R$_f$=0.36.

Intermediate 69

3-Amino-1-(2,2-dimethylethoxycarbonylmethyl)-2,4-dioxo-5-phenyl-2,3,4,5-tetrahydro-1H-1,5-benzodiazepine A solution of the intermediate 68 (0.354 g) in a mixture of ethanol (10 ml) and ethyl acetate (2 ml) was stirred under hydrogen, at 1 atm., in presence of 5% Pd/CaCO$_3$ (0.183 g), at 23°, for 3 h, then more 5% Pd/CaCO$_3$ (0.183 g) was added and the reaction stirred for 15 h. The catalyst was filtered off on a pad of celite, washing with dichloromethane (9 ml) and methanol (5 ml) and the organic layer was concentrated "in vacuo". The crude product was purified by flash chromatography (eluting with DCM-methanol 96:4) to give the title compound as a white foam (0.33 g). T.l.c. DCM-methanol (95:5), R$_f$=0.5.

Intermediate 70

4,5-Dichloro-2-(2,2-dimethylethoxy-carbonyl) amino-diphenylamine

Di-tert-butyl dicarbonate (13.98 g) and triethylamine (25 ml) were added to the solution of 4,5-dichloro-2-amino-diphenylamine (14.7 g) in dichloromethane (200 ml) at 0°. The mixture was stirred at 0° for 1 h, then at 23° for 24 h; a further amount of di-tert-butyl dicarbonate (2.8 g) was added and stirring was continued at 23° for 80 h. The reaction mixture was diluted with water (200 ml), acidified at pH=2 with conc. hydrochloric acid and extracted with dichloromethane (3×200 ml); the organic layer was washed with brine (300 ml), dried and evaporated to give the crude compound which was purified by flash chromatography (eluting with CH/EA 8/2 then 1/1) to give the title compound as a brown glass (5.54 g). T.l.c. CH-EA (7:3), $R_f$=0.66.

Intermediate 71

4,5-Dichloro-2-(2,2-dimethylethoxy-carbonyl) amino-1-[2-(1-ethoxycarbonyl-2-oxo)ethyl] amino-diphenylamine Ethyl malonyl chloride (2.35 ml) pyridine (1.85 ml) and 4-dimethylaminopyridine 947.4 mg) were added to the suspension of intermediate 70 (5.4 g) in dry toluene (130 ml). The mixture was stirred at 80° under a nitrogen atmosphere for 18 h, then a further amount of ethyl malonyl chloride (0.65 ml) and pyridine (0.55 ml) were added and stirring was continued at 110° for 5 h. The reaction mixture was cooled to 23°, the dark tar filtered off and the filtrate diluted with EA (200 ml), washed with a saturated sodium bicarbonate solution (3×200 ml) brine (200 ml), dried and evaporated to give the crude compound which was purified by flash chromatography (eluting with CH/EA 8/2 then 1/1) to give the title compound as a dark yellow foam (2.51 g). T.l.c. CH-EA (8:2), $R_f$=0.27.

Intermediate 72

7,8-Dichloro-2,4-dioxo-5-phenyl-2,3,4,5-tetrahydro-1H-1,5-benzodiazepine

Concentrated hydrochloric acid (9 ml) was added to the suspension of intermediate 71 (3.53 g) in ethanol (12.5 ml). The mixture was stirred at 23° for 18 h, then diluted with EA (200 ml), washed with water (2×100 ml), saturated sodium bicarbonate solution (2×100 ml) brine (100 ml), dried and evaporated to give the crude compound which was purified by flash chromatography (eluting with CH/EA 7/3, then 1/1) to give the title compound as a white foam (0.57 g). T.l.c. CH-EA (6:4), $R_f$=0.23.

Intermediate 73

7,8-Dichloro-2,4-Dioxo-1-(3-methyl-2-oxo-butyl)-5-phenyl-2,3,4,5-tetrahydro-1H-1,5-benzodiazepine Sodium hydride 80% dispersion in oil (0.070 g) was added portionwise to a solution of the intermediate 72 (0.570 g) in dry dimethylformamide (12 ml). The reaction mixture was stirred at 23° for 15 min, then a solution of 1-bromomethyl-2-oxo-butane (0.360 g) in dry dimethylformamide (3 ml) was added and stirring continued for 7 h at 140°. The reaction mixture was then diluted with water (100 ml), extracted with ethyl acetate (3×70 ml), washed with brine (2×50 ml), dried and concentrated in vacuo to give an oil which was purified by flash chromatography (eluting with CH-EA 60:40) to give the title compound as a white foam (0.160 g). T.l.c. CH-EA (6:4), Rf=0.31.

Intermediate 74

3-Azido-7,8-dichloro 2,4-Dioxo-1-(3-methyl-2-oxo-butyl)-5-phenyl-2,3,4,5-tetrahydro-1H-1,5-benzodiazepine A solution of the intermediate 73 (0.150 g) in THF (4 ml) was added to potassium tert-butoxide (0.054 g) in THF (2 ml) cooled to −78°. The reaction mixture was stirred for 30 min, then a cooled (−78°) solution of 2,4,6-triisopropylbenzenesulphonyl azide (0.160 g) in dry THF (4 ml) was added. After 5 min glacial acetic acid (0.021 ml) was added and the solution was allowed to warm to 23° and stirred for 24 h. The reaction mixture was diluted with ethyl acetate (25 ml) and washed with brine (25 ml), saturated sodium hydrogen carbonate solution (50 ml) and brine (25 ml). The combined organic extracts were dried and concentrated in vacuo to give an oil (0.28 g). Purification by flash chromatography (eluting with CH-EA 70:30) gave the title compound as a white foam (0.074 g) after trituration with diethylether T.l.c. CH-EA (60:40), Rf=0.67.

Intermediate 75

3-Amino-7,8-dichloro-2,4-Dioxo-1-(3-methyl-2-oxo-but-1-yl)-5-phenyl-2,3,4,5-tetrahydro-1H-1,5-benzodiazepine 1,3-Propanedithiol (0.05 ml) and triethylamine (0.1 ml) were added to a solution of the intermediate 74 (0.063 g) in dichloromethane/methanol 1/1 and the reaction mixture was stirred at 23° for 20 h. A further amount of 1,3-propanedithiol (0.03 ml) was added and stirring continued for 2 h; the reaction mixture was acidified with 10% hydrochloric acid solution (25 ml), extracted with diethylether (3×30 ml), the aqueous phase was basified with 10% sodium hydroxide solution (30 ml), extracted with diethylether (4×30 ml), washed with brine (30 ml), dried and evaporated in vacuo to give the title compound as a white wax (0.040 g). T.l.c. EA-methanol (9:1), Rf=0.66.

Intermediate 76

2-(3-hydroxy-1-propyl)amino-diphenylamine

A mixture of 3-bromo-1-propanol (1.47 ml), 2-aminodiphenylamine (3.0 g) and sodium iodide (2.44 g) in dimethylformamide (30 ml) was heated to 130° for 8 h under a nitrogen atmosphere. The solution was then cooled to room temperature, diluted with water (40 ml) and extracted with ethyl acetate (3×50 ml). The combined organic extracts were washed with brine (100 ml), dried and concentrated in vacuo to an oil, which was purified by flash chromatography (eluting with CH-EA 7:3) to give the title compound as a yellow oil (2.25 g). T.l.c. CH-EA (1:1), Rf 0.49.

Intermediate 77

2-(3-tert-butyldimethylsilyloxy-1-propyl)amino-diphenylamine

A solution of the intermediate 76 (1.8 g), tert-butyldimethylsilyl chloride (1.36 g) and imidazole (1.285 g) in dry dimethylformamide (5 ml) was stirred at 23° for 18 h. The solution was diluted with water (15 ml) and extracted with ethyl acetate (30 ml). The organic layer was washed with brine (30 ml), dried and concentrated in vacuo to an oil, which was purified by flash chromatography (eluting with CH-EA 9:1) to give the title compound as a yellow oil (1.6 g). T.l.c. CH-EA (8:2), Rf 0.82.

Intermediate 78

4-Dioxo-1-(3-hydroxy-1-propyl)-5-phenyl-3-phenylhydrazono-2,3,4,5-tetrahydro-1H-1,5-benzodiazepine The intermediate 77 (1.5 g) and the 2-phenylhydrazono-malonyldichloride (1.25 g) were each taken up in THF (15 ml) and dropped in a flask containing THF (10 ml) under a nitrogen atmosphere. After complete addition the solution was heated to 85° for 2 h. The solution was concentrated in vacuo to a foam, which was purified by flash chromatography (eluting in gradient from CH-EA 9:1 to EA) to give the title compound as a yellow solid (1.05 g). M.p. 113°–5° CH-EA (2:8), Rf 0.48.

Intermediate 79

3-Amino-2,4-dioxo-1-(3-hydroxy-1-propyl)-5-phenyl-2,3,4,5-tetrahydro-1H-1,5-benzodiazepine Zinc dust was added to a solution of the intermediate 78 (0.99 g) in glacial acetic acid (10 ml). The mixture was stirred at 23° for 1 h, then decanted from zinc. The filtrate was basified with a 10% sodium hydroxide solution until pH=9 and the mixture extracted with ethyl acetate (2×50 ml). The combined organic extracts were washed with brine (80 ml), dried and concentrated in vacuo to an oil which was purified by flash chromatography (eluting in gradient from CH-EA 2:8 to EA-MeOH 85:15) to give the title compound as a white foam (0.35 g). M.p. 55°–8°. T.l.c. EA-MeOH (85:15), Rf 0.29.

Intermediate 80

2-Amino-4-chlorodiphenylamine

Potassium carbonate (13 g) and sodium hydrosulphite (11.4 g) were added portionwise over 3 hour to a suspension of 4-chloro-2-nitrodiphenylamine (3.6 g) in 95% ethanol (100 ml) and water (100 ml). The mixture was stirred at 23° for 20 h. The reaction mixture was then acidified to pH=4 with conc. hydrochloric acid (20 ml); then 10% solution of sodium hydroxide (80 ml) was added until pH=10 and the solution extracted with ethyl acetate (2×150 ml). The combined organic extracts were washed with brine (2×150 ml), dried and concentrated in vacuo to give the crude compound as a yellow solid (7.8 g) which was purified by flash chromatography (eluting with CH-EA 90:10 then 70:30) to give the title compound as a yellow foam (2.37 g). T.l.c. CH-EA (1:1), Rf 0.66.

Intermediate 81

4-Chloro-2-(3-methylbut-1-yl)amino-diphenylamine

Bromo 3-methylbutane (0.62 ml) was added to a solution of the intermediate 80 (1.00 g) and sodium iodide (0.7 g) in dimethylformamide (40 ml) under a nitrogen atmosphere. The solution was stirred at 120° for 12 h, then cooled at 23° C., diluted with ethyl acetate (150 ml) and washed with brine (3×100 ml). The combined organic extracts were dried and concentrated in vacuo to give an oil, which was purified by flash chromatography (eluting with CH-EA 95:5) to give the title compound as a yellow oil (0.74 g). T.l.c. CH-EA (1:1), Rf 0.76.

Intermediate 82

8-Chloro-2,4-Dioxo-1-(3-methylbut-1-yl)-5-phenyl-3-phenylhydrazono-2,3,4,5-tetrahydro-1H-1,5-benzodiazepine The intermediate 81 (0.74 g) and the 2-phenylhydrazono-malonyldichloride (0.75 g) were each taken up in THF (15 ml) and dropped in a flask containing THF (20 ml) maintained at 0° under a nitrogen atmosphere. After complete addition, the solution was allowed to warm to 23° C., stirred for 30 min., then heated at 60° for 2 h. The solution was diluted with ethyl acetate (120 ml), washed with brine (2×100 ml), dried and concentrated in vacuo to give an oil, which was purified by flash chromatography (eluting with CH-EA 95:5, increasing polarity to 70:30) to give the title compound as a yellow solid (0.91 g). T.l.c. CH-EA (1:1), R.f 0.68

Intermediate 83

3-Amino-8-chloro-2,4-dioxo-1-(3-methylbut-1-yl)-5-phenyl-2,3,4,5-tetrahydro-1H-1,5-benzodiazepine To the solution of intermediate 82 (0.9 g) in glacial acetic acid (20 ml) at 0°, zinc dust (1.14 g) was added portionwise. The mixture was stirred at 23° for 1 h, then decanted from zinc, washed with ethyl acetate (150 ml) and then with 10% sodium hydroxide (150 ml) and brine (100 ml). The combined organic extracts were dried and concentrated in vacuo to an oil which was purified by flash chromatography (eluting in gradient from CH-EA 1:1 to EA-methanol 27:3) to give the title compound (0.53 g). T.l.c. EA-methanol (27:3), Rf 0.6.

Intermediate 84

2-amino-4-Fluoro-diphenylamine

Potassium carbonate (9.3 g) and sodium hydrosulfite (8.2 g) were added portionwise over 3 hour to a suspension of 4-fluoro-2-nitrodiphenylamine (2.4 g) in 95% ethanol (70 ml) and water (70 ml). The mixture was stirred at 23° for 20 h. The reaction mixture was the n acidified to pH=4 with conc. hydrochloric acid (15 ml), then 10% solution of sodium hydroxide (50 ml) was added until pH=10, and the concentrated solution extracted with ethyl acetate (2×100 ml). The combined organic extracts were washed with brine (2×80 ml), dried and concentrated in vacuo to give the crude compound which was purified by flash chromatography (eluting with CH-EA 90:10 then 80:20) to give the title compound as a yellow foam (1.44 g). T.l.c. CH-EA (1:1), Rf 0.72.

Intermediate 85

4-Fluoro-2-(3-methylbut-1-yl)amino-diphenylamine

1-Bromo 3-methylbutane (1.0 ml) was added to a solution of the intermediate 84 (1.44 g) and sodium iodide (1.1 g) in dimethylformamide (60 ml) under a nitrogen atmosphere. The solution was stirred at 120° for 9 h; the reaction mixture was diluted with ethyl acetate (300 ml) and washed with brine (3×150 ml). The combined organic extracts were dried and concentrated in vacuo to give an oil, which was purified by flash chromatography (eluting with CH-EA 95:5) to give the title compound as a yellow oil (0.96 g). T.l.c. CH-EA (1:1), Rf 0.74.

Intermediate 86

2,4-Dioxo-8-fluoro-1-(3-methylbut-1-yl)-5-phenyl-3-phenylhydrazono-2,3,4,5-tetrahydro-1H, 1,5-benzodiazepine The intermediate 85 (0.96 g) and 2-phenylhydrazonomalonyldichloride (1.01 g) were each taken up in THF (15 ml) and dropped in a flask containing THF (40 ml) maintained at –0° under a nitrogen atmosphere. After complete addition the solution was allowed to warm at 23° C., stirred for 30 min., then heated at 60° for 2 h. The solution was diluted with ethyl acetate (120 ml), washed with brine (2×100 ml), dried and concentrated in vacuo to give an oil, which was purified by flash chromatography (eluting with CH-EA 95:5, increasing polarity to 80:20) to give the title compound as a yellow solid (1.3 g). T.l.c. CH-EA (1:1), Rf 0.74.

Intermediate 87

3-Amino-2,4-dioxo-8-Fluoro 1-(3-methylbut-1-yl)-5-phenyl-2,3,4,5-tetrahydro-1H-1,5-benzodiazepine To the solution of the intermediate 86 (1.3 g) in glacial acetic acid (20 ml) at 0°, zinc dust (1.2 g) was added portionwise. The mixture was stirred at 23° for 1 h, then decanted from zinc, washed with ethyl acetate (150 ml) and then with 10% sodium hydroxide (150 ml) and brine (100 ml). The combined organic extracts were dried and concentrated in vacuo to give an oil which was purified by flash chromatography (eluting in gradient from CH-EA 1:1 to EA-methanol 80:20) to give the title compound (0.72 g). T.l.c. EA-methanol (27:3), Rf 0.47.

EXAMPLE 1

2,4-Dioxo-1-(3-methylbut-1-yl)-5-phenyl-3-(phenyloxycarbonylamino)-2,3,4,5-tetrahydro-1H-1,5-benzodiazepine Pyridine (0.153 ml) and phenyl chloroformate (0.24 ml) were added to a solution of the intermediate 3 (0.32 g) in dichloromethane (20 ml) under a nitrogen atmosphere. The resulting solution was stirred at 23° for 30 min, then washed with a 1% solution of hydrochloric acid (2×20 ml), a 5% solution of sodium hydrogen carbonate (2×20 ml) and brine (20 ml). The organic layer was dried and concentrated in vacuo to a solid which was triturated with acetonitrile to give the title compound as a white solid (0.29 g). M.p. 205°–6°. T.l.c. CH-EA, Rf=0.73, IR (nujol): 3252 (NH), 1734, 1695 and 1682 (C=O) cm$^{-1}$; $^1$H-NMR: 7.48-7.38 (m); 7.38-7.30 (m); 7.24-7.13 (m); 6.99 (dd); 6.47 (d); 5.12 (d); 4.57 (m); 3.70 (m); 1:64-1.42 (m); 0.93 (d); 0.90 (d).

EXAMPLE 2

1-(3,3-Dimethylbut-1-yl)-2,4-dioxo-5-phenyl-3-(phenyloxycarbonylamino)-2,3,4,5-tetrahydro-1H-1,5-benzodiazepine Pyridine (0.46 ml) and phenyl chloroformate (0.7 ml) were added to a solution of the intermediate 3 (1.0 g) in dichloromethane (50 ml) under a nitrogen atmosphere. The resulting solution was stirred at 23° for 30 min, then washed with a 1% solution of hydrochloric acid (20 ml), a 5% solution of sodium hydrogen carbonate (20 ml) and brine (20 ml). The organic layer was dried and concentrated in vacuo to a solid which was triturated with acetonitrile to give the title compound as a white solid (1.2 g). M.p. 170°–2°. T.l.c. CH-EA, Rf=0.80. IR (nujol): 3250 (NH), 1736 and 1695 (C=O), 1593 (C=C) cm$^1$; $^1$H-NMR: 7.46-7.14 (m); 7.10 (dd); 6.46 (d); 5.12 (d); 4.94 (m); 3.71 (m); 1.5 (m); 0.95 (d).

EXAMPLE 3

3-[3-(N,N-dimethylamino)phenyloxycarbonylamino-2,4-dioxo-1-(3-methylbut-1-yl)-5-phenyl-2,3,4,5-tetrahydro-1H-1,5-benzodiazepine Pyridine (0.143 ml) and the intermediate 10 (0.55 g) were added to a solution of the intermediate 3 (0.3 g) in dichloromethane (10 ml) under a nitrogen atmosphere. The resulting solution was stirred at 23° for 30 min, then washed with a 5% solution of hydrochloric acid (15 ml), a 5% solution of sodium hydrogen carbonate (15 ml) and brine (15 ml). The organic layer was dried and concentrated in vacuo to a solid which was triturated with acetonitrile to give the title compound as a white solid (0.29 g). M.p. 205°–6°. T.l.c. CH-EA, Rf=0.73, IR (nujol): 3314 (NH), 1728, 1705 and 1666 (C=O), 1612 (C=C) cm$^{-1}$; $^1$H-NMR: 7.45-7.05 (m); 6.99 (dd); 6.6-6.46 (m); 6.42 (d); 5.13 (d); 4.55 (m); 3.69 (m); 2.9 (s); 1.62-1.4 (m); 0.92 (d); 0.89 (d).

EXAMPLE 4

3-[3-(N,N-dimethylamino)phenyloxycarbonylamino-2,4-dioxo-1-(3-methyl-2-oxo)but-1-yl)-5-phenyl-2,3,4,5-tetrahydro-1H-1,5-benzodiazepine Pyridine (0.055 ml) and the intermediate 10 (0.135 g) were added to a solution of the intermediate 9 (0.12 g) in dichloromethane (10 ml) under a nitrogen atmosphere. The resulting solution was stirred at 23° for 30 min, then washed with a 5% solution of hydrochloric acid (15 ml), a 5% solution of sodium hydrogen carbonate (15 ml) and brine (20 ml). The organic layer was dried and concentrated in vacuo to a foam which was triturated with diethyl ether to give the title compound as a beige solid (0.082 g). M.p. 205°–6°. T.l.c. CH-EA, Rf=0.50. IR (nujol): 3315 (NH, 1726, 1703 and 1668 (C=O), 1610 (C=C) cm$^{-1}$; $^1$H-NMR: 7.46-7.10 (m); 7.00 (d); 6.6-6.46 (m); 6.40 (d); 5.24 (d); 5.09 (d); 4.69 (m); 2.9 (s); 2.74 (m); 1.19 (d); 1.17 (d).

EXAMPLE 5

1-(Adamant-2-yl)-3-[3-(N,N-dimethylamino) phenyloxycarbonylamino]-2,4-dioxo-5-phenyl-2,3,4,5-tetrahydro-1H-1,5-benzodiazepine Pyridine (0.04 ml) and the intermediate 10 (0.1 g) were added to a solution of the intermediate 13 (0.1 g) in dichloromethane (5 ml) under a nitrogen atmosphere. The resulting solution was stirred at 23° for 30 min, then diluted with further dichloromethane (10 ml), washed with a 5% solution of hydrochloric acid (20 ml), a 5% solution of sodium hydrogen carbonate (20 ml) and brine (20 ml). The organic layer was dried and concentrated in vacuo to a foam which was triturated with EE and P to give the title compound as a beige solid (0.0658). M.p. 136°–70° (dec). T.l.c. CH-EA (1:1), Rf 0.68. IR (nujol): 3410 (NH), 1744, 1707 and 1676 (C=O), 1610 (C=C) cm$^{-1}$; $^1$H-NMR 7.40 (d); 7.38-7.12 (m); 7.1-6.96 (m); 6.56-6.48 (d); 6.38 (d); 5.24 (d); 4.55 (sa); 2.99 (sa); 2.92 (s); 2.32 (sa); 1.9-1.1 (m).

EXAMPLE 6

2,4-Dioxo-5-(2-fluorophenyl)-1-(3-methylbut-1-yl)-3(phenyloxycarbonylamino)-2,3,4,5-tetrahydro-1H-1,5-benzodiazepine Pyridine (0.137 ml) and phenyl chloroformate (0.21 ml) were added to a solution of intermediate 15 (0.38) in dichloromethane (15 ml) under a nitrogen atmosphere. The resulting solution was stirred at 23° for 30 mm, then washed with a 1% solution of hydrochloric acid (15 ml), a 5% solution of sodium hydrogen carbonate (15 ml) and brine (20 ml). The organic layer was dried and concentrated in vacuo to a solid which was triturated with ethyl acetate to give the title compound as a white solid (0.38). M.p. 226°–7°. T.l.c. CH-EA (1:1), Rf=0.75. IR (nujol): 3275 (NH), 1734, 1707 and 1684 (C=O), 1593 (C=C) cm$^{-1}$; $^1$H-NMR: 7.46 (dd); 7.44-7.3 (m); 7.27-7.14 (m); 7.00 (dd); 6.455 (d); 6.2 (d); 5.172 (d); 4.550-4.473 (m); 3.772-3.677 (m); 1.6 (m); 1.56-1.46 (m); 0.938 (d); 0.924 (d).

EXAMPLE 7

1-(3,3-Dimethylbut-1-yl)-2,4-dioxo-5-(2-fluorophenyl)-3(phenyloxycarbonylamino))-2,3,4,5-tetrahydro-1H-1,5-benzodiazepine Pyridine (0.64 ml) and phenyl chloroformate (1.0 ml) were added to a solution of the intermediate 19 (1.58) in dichloromethane (100 ml) under a nitrogen atmosphere. The resulting solution was stirred at 23° for 30 min, then washed with a 1% solution of hydrochloric acid (2×70 ml), a 5% solution of sodium hydrogen carbonate (2×70 ml) and brine (100 ml). The organic layer was dried and concentrated in vacuo to a solid which was triturated with EE to give the title compound as a white solid (1.4 g). M.p. 199°–200°. T.l.c. CH-EA (1:1), Rf=0.82. IR (nujol): 3290 (NH), 1740, 1707 and 1686 (C=O), 1593 (C=C) cm$^{-1}$; $^1$H-NMR: 7.5-7.3 (m); 7.3-7.1 (m); 6.997 (dd); 6.446 (d); 5.169 (d); 4.483-4.407 (m); 3.780-3.709 (m); 1.524 (m); 0.957 (d).

EXAMPLE 8

3-[3-(N,N-dimethylamino)phenyloxycarbonylamino]-2,4-dioxo-5-(2-fluorophenyl)-1-(3-methylbut-1-yl)-2,3,4,5-tetrahydro-1H-1,5-benzodiazepine Pyridine (0.135 ml) and the intermediate 10 (0.34 g) were added to a solution of the intermediate 16 (0.3 g) in dichloromethane (10 ml) under a nitrogen atmosphere. The resulting solution was stirred at 23° for 30 min, then washed with a 1% solution of hydrochloric acid (2×5 ml), a 5% solution of sodium hydrogen carbonate (2×5 ml) and brine (20 ml). The organic layer was dried and concentrated in vacuo to a foam which was triturated with EE to give the title compound as a beige solid (0.33 g). M.p. 193°–4°. T.l.c. CH-EA (1:1), Rf=0.56. IR (nujol): 3312 (NH), 1728, 1707 and 1666 (C=O), 1610 (C=C) cm$^{-1}$; $^1$H-NMR: 7.5-7.1 (m); 6.98 (dd); 6.6-6.4 (m); 6.48 (s); 6.41 (d); 5.18 (d); 4.47 (m); 3.71 (m); 2.93 (s); 1.65-1.45 (m); 0.93 (d); 0.91. (d).

EXAMPLE 9

3-[3-(N,N-dimethylamino)phenyloxycarbonylamino]-1-(3,3-dimethylbut-1-yl)-2,4-dioxo-5-(2-fluorophenyl)-2,3,4,5-tetrahydro-1H-1,5-benzodiazepine Pyridine (0.13 ml) and the intermediate 10 (0.324 g) were added to a solution of the intermediate 19 (0.3 g) in dichloromethane (10 ml) under a nitrogen atmosphere. The resulting solution was stirred at 23° for 30 min, then washed with a 5% solution of hydrochloric acid (15 ml), a 5% solution of sodium hydrogen carbonate (15 ml) and brine (15 ml). The organic layer was dried and concentrated in vacuo to a solid which was triturated with diethyl ether to give the title compound as a beige solid (0.29 g). M.p. 160°–1°. T.l.c. CH-EA (1:1), Rf=0.56. IR (nujol): 3323 (NH), 1709 and 1666 (C=O), 1612 (C=C) cm$^{-1}$; $^1$H-NMR: 7.5-7.1 (m); 6.98 (dd); 6.6-6.4 (m): 6.41 (d); 5.19 (d); 4.44 (m); 3.73 (m); 2.92 (s); 1.6-1.4 (m); 0.95 (s).

EXAMPLE 10

1-(2-Adamantylethyl)-3-[3-(N,N-dimethylamino) phenyloxycarbonyl]amino-2,4-dioxo-5-phenyl-2,3,4,5-tetrahydro-1H-1,5-benzodiazepine Pyridine (0.037 ml) and 3-(dimethylamino)phenylchloroformate (0.093 g) were added to a solution of the intermediate 28 (0.1 g) in dichloromethane (8 ml) under a nitrogen atmosphere. The solution was stirred at 23° for 30 min., then washed with 5% hydrochloric acid solution (2×7 ml), 5% sodium hydrogen carbonate solution (2×10 ml) and brine (2×7 ml).The combined organic extracts were dried and evaporated under reduced pressure; the crude material was triturated with diethyl ether/petroleum, to give the title compound (0.095 g) as a solid. M.p. 188°–9°. T.l.c. CH-EA (70:30), Rf0.32. IR: 3277 (NH), 1736, 1695 and 1680 (C=O) cm$^{-1}$; $^1$H-NMR: 7.50-7.14 (m); 7.01 (m); 6.60-6.43 (m); 5.16(d); 4.54 (m); 3.71 (m); 2.94 (s); 1.88-1.48 (m).

EXAMPLE 11

3-[3-(N,N-dimethylamino)phenyloxycarbonylamino]-2,4-dioxo-7-fluoro-1-(3-methylbut-1-yl)-5-phenyl-2,3,4,5-tetrahydro-1H-1,5-benzodiazepine Pyridine (0.036 ml) and 3-(N,N-dimethylamino)phenyl chloroformate (0.08 added to a solution of the intermediate 31 (0.078 g) in dichloromethane (15 ml) under a nitrogen atmosphere. The resulting solution was stirred at 23° for 30 min, then washed with a 5% solution of hydrochloric acid (30 ml), a 5% solution of sodium hydrogen (30 ml) and brine (30 ml). The organic layer was dried concentrated in vacuo to a foam (105 mg) This material was triturated with diethylether to give the title compound as a pink solid (0.08 g) M.p. 229°–230°. T.l.c. CH-EA (2:1), Rf=0.35. IR (nujol): 3265 (NH), 1734, 1697 and 1674 (C=O) cm$^{-1}$; $^1$H-NMR: 7.50-7.32 (m); 7.24-7.13 (m); 7.060 (m); 6.68 (dd); 6.58-6.52 (m); 6.50 (m); 6.42 (d); 5.14 (d); 4.56 (m); 3.62 (m); 2.930 (s); 1.66-1.4 (m); 0.950-0.91(dd).

EXAMPLE 12

7,8-Dichloro-3[3-(N,N-dimethylamino) phenyloxycarbonylamino]-2,4-dioxo-1-(3-methylbut-1-yl)-5-phenyl-2,3,4,5-tetrahydro-1H-1,5-benzodiazepine Pyridine (0.06 ml) and 3-(N,N-dimethylamino)phenyl chloroformate (0.147 g) were added to a solution of the intermediate 30 (0.15 g) in dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a solid which was triturated with diethyl ether/petroleum to give the title compound as a beige solid (0.14 g). M.p. 163°–4°. T.l.c. CH-EA (1:1), Rf=0.80. IR (nujol): 1740, 1720 and 1680 (C=O) cm$^{-1}$; $^1$H-NMR: 7.53 (m); 7.47-7.37 (m); 7.2-7.1 (m); 7.06 (m); 6.6-6.47 (m); 6.38 (d); 5.10 (d); 4.56 (m); 3.63 (m); 2.92 (s); 1.6-1.4 (m); 0.93 (d); 0.91 (d). The title compound was resolved into pure enantiomers by using preparative HPLC (Pirkle D-DNBPG; Hexane/DCM/isopropanol 74/25/1) to give the (+) 7,8-Dichloro-3-[3-(N,N-dimethylamino)phenyloxycarbonylamino]-2,4-dioxo-1-(3-methylbut-1-yl)-5-phenyl-2,3,4,5-tetrahydro-1H-1,5-benzodiazepine enantiomer (57.5 mg); alpha-D=+79.4 (CHCl$_3$); IR (nujol): 1744, 1713 and 1680 (C=O), 1610 (C=C); $^1$H-NMR: 7.53 (bs), 7.50-7.34 (m), 7.20-7.15 (m), 7.05 (bs), 6.60-6.46 (m), 6.39 (d), 5.10 (d), 4.6-4.5 (m), 3.71-3.5 (m), 2.9 (s), 1.7-1.4 (m) 0.93 (d), 0.90 (d); and the corresponding (–) enantiomer (109 mg); alpha-D=–41.3 (CHCl$_3$); IR (nujol): 1744, 1713 and 1680 (C=O), 1610 (C=C); $^1$H-NMR: 7.54 (bs), 7.50-7.34 (m), 7.20-7.16 (m), 7.069 (bs), 6.60-6.46 gm), 6.39 9 d0 , 5.11 (d), 4.64-4.50 (m), 3.71 -3.56 (m), 2.929 (s), 1.62-1.44 (m), 0.94 (d), 0.92 (d).

EXAMPLE 13

1-2-cyclopentylethyl)-2,4-dioxo-(2-fluorophenyl)-3-(phenyloxycarbonylamino)-2,3,4,5-tetrahydro-1H-1,5-benzodiazepine Pyridine (0.051 ml) and phenyl chloroformate (0.079 ml) were added to a solution of the intermediate 34 (0.120 g) in dichloromethane (8 ml) under a nitrogen atmosphere. The resulting solution was stiffed at 23° for 30 min., diluted with dichloromethane (35 ml), washed with water (15 ml), 1% solution of hydrochloric acid (15 ml), a 5% solution of sodium hydrogen carbonate (15 ml) and brine (20 ml). The organic layer was dried and concentrated in vacuo to a solid which was triturated with acetonitrile (5 ml) to give the title compound as a white solid (0.094 g). Mp 205°–207°. T.l.c. CH-EA (1:1), Rf 0.68. IR: 3280-(NH), 1736, 1709 and 1682 (C=O) cm$^{-1}$; $^1$H-NMR: 7.46 (dd); 7.44-7.28 (m); 7.28-7.08 (m); 6.99 (dd); 6.46 (d); 5.17 (d); 4.47 (m); 3.72 m); 1.86-1.70 (m); 1.70-1.44 (m); 1.12 (m).

EXAMPLE 14

1-(Bicyclo[2.2.1]-5-heptene-2-ylmethyl)-2,4-dioxo-3-phenyloxycarbonylamino-2,3,4,5-tetrahydro-1H-1,5-benzodiazepine Phenylchloroformate (0.048 ml) and pyridine (0.035 ml) were added to a solution of the intermediate 37 (0.071 g) in dry dichloromethane (5 ml). The mixture was stirred at 23°, under nitrogen, for 1 h, then it was diluted with dichloromethane (15 ml) and washed with a 10% hydrochloric acid solution (10 ml) and brine (20 ml). The organic layer was dried, concentrated in vacuo and triturated with diethyl ether to give the title compound (0.0603 g) as an off-white solid. Mp. 200°–2°. T.l.c. (CH-EA 7:3) R$_f$ 0.39. IR: 3273 (NH), 1738 and 1695 (C=O) cm$^{-1}$; NMR: 7.50-7.10 (m); 7.00 (dd); 6.56 (m); 6.44 (m); 6.55-6.44 (m); 6.24-6.14 (m); 6.06-6.00 (m), 5.90-5.64 (m+m); 5.18 (m), 5.02 (m); 4.74-4.60 (m); 4.40-4.30 (m); 3.86-3.72 (m); 3.52-3.34 (m); 2.85-0.70 (m).

EXAMPLE 15

1-(Bicyclo[2.2.1]-2-heptylmethyl)-2,4-dioxo-3-phenyloxycarbonylamino-2,3,4,5-tetrahydro-1H-1,5-benzodiazepine Phenylchloroformate (0.061 ml) and pyridine (0.045 ml) were added to a solution of the intermediate 38 (0.0913 g) in dry dichloromethane (5 ml). The mixture was stirred at 23° for 1 h, diluted with dichloromethane (20 ml) and washed with a 10% hydrochloric acid solution (20 ml) and brine (20 ml), dried and concentrated in vacuo. The residue was triturated with diethyl ether to give the title compound (0.071 g) as an off-white solid. M.p. 203°–5°. T.l.c. (CH-EA 7:3) Rf 0.42. IR: 3261 (NH), 1738, 1695 (C=O), 1600 (C=C); $^1$H-NMR: 7.5-7.10 (m); 6.99 (m); 6.48 (m); 5.14 (d); 5.02 (d); 4.76 (d); 4.38 (d); 3.92 (m); 3.35 (m); 2.3-0.60 (m).

EXAMPLE 16

1-[Bicyclo[2.2.1]-2-heptyl]-3-[3-(N,N-dimethylamino)phenyloxycarbonyl]amino-2,4-dioxo-5-phenyl-2,3,4,5-tetrahydro-1H-1,5-benzodiazepine Pyridine (0.069 ml) and 3-(N,N-dimethylamino)phenyl chloroformate (0.165 g) were added to a solution of the intermediate 41 (0.15 g) in dry dichloromethane (10 ml) under a nitrogen atmosphere. The solution was stirred at 23° for 30 mm, then washed with a 5% hydrochloric acid solution (30 ml), a 5% sodium hydrogen carbonate solution (30 ml) and brine (30 ml). The organic layer was dried and concentrated in vacuo to a solid which was triturated with petroleum-diethyl ether 2:1 (6 ml) to give the title compound as a beige solid (0.11 g). M.p. 125°–6°. T.l.c. CH-EA (1:1), Rf 0.78. IR: 3306 (NH), 1747 and 1705 (C=O) cm$^{-1}$; $^1$H-NMR: 7.47-7.15 (m); 6.99 (m); 6.6-6.4 (m); 6.37 (t); 5.12 (m); 4.49 (m); 3.51 (s); 2.65 (m); 2.5 (m); 2.29 (m); 2.19 (m); 1.97 (m); 1.6-0.8 (m).

EXAMPLE 17

1-(2-Adamantylmethyl)-2,4-dioxo-5-phenyl-3-phenyloxycarbonylamino-2,3,4,5-tetrahydro-1H-1,5-benzodiazepine Pyridine (0.077 ml) and phenyl chloroformate (0.12 ml) were added to a solution of the intermediate 44 (0.2 g) in dry dichloromethane (10 ml) under a nitrogen atmosphere. The solution was stirred at 23° for 30 min, then washed with a 5% hydrochloric acid solution (20 ml), a 5% sodium hydrogen carbonate solution (20 ml) and brine (20 ml). The organic layer was dried and concentrated in vacuo to a solid which was triturated with petroleum-diethyl ether 5:1 (12 ml) to give the title compound as a beige solid (0.17 g). M.p. 167°–8°. T.l.c. CH-EA (7:3), Rf 0.48. IR: 3260 (NH), 1726, 1699 and 1672 (C=O) cm$^{-1}$; $^1$H-NMR: 7.49 (m); (m); 1.9-1.5 (m).

EXAMPLE 18

1-(2-Adamantylmethyl)-3-[3-(N,N-dimethylamino)phenyloxycarbonyl]amino-2,4-dioxo-5-phenyl-2,3,4,5-tetrahydro-1H-1,5-benzodiazepine Pyridine (0.077 ml) and 3-(N,N-dimethylamino)phenyl chloroformate (0.19 g) were added to a solution of the intermediate 44 (0.2 g) in dry dichloromethane (10 ml)

under a nitrogen atmosphere. The solution was stirred at 23° for 30 min, then washed with a 5% hydrochloric acid solution (20 ml), a 5% sodium hydrogen carbonate solution (20 ml) and brine (20 ml). The organic layer was dried and concentrated in vacuo to a solid which was triturated with petroleum-diethyl ether 5:1 (12 ml) to give the title compound as a beige solid (0.18 g). M.p. 184°5°. T.l.c. CH-EA (7:3), Rf0.38. IR: 3355 and 3298 (NH), 1705 and 1668 (C=O) cm$^{-1}$; $^1$H-NMR: 7.48 (m); 7.44-7.32 (m); 6.97 (m); 6.9-6.47 (m); 6.40 (d); 5.13 (d); 5.08 (m); 3.61 (m); 2.93 (s); 2.08 (m); 1.9-1.46.

EXAMPLE 19

1-(Adamantylmethyl)-2,4-dioxo-3-phenyloxycarbonylamino-5-phenyl-2,3,4,5-tetrahydro-1H-1,5-benzodiazepine Pyridine (0.25 ml) and phenyl chloroformate (0.33 ml) were added to a solution of the intermediate 47 (0.555 g) in dichlorometane (10 ml) under a nitrogen atmosphere. The resulting solution was stirred at 23° for 20 h, then diluted with DCM (10 ml) and washed with brine (15 ml). The organic layer was dried and concentrated in vacuo to a solid (0.74 g) which was purified by flash chromatography with CH-EA 9/1 as eluent to give the title compound as a white solid (0.62 g). M.p. 205°–7°. T.l.c. CH-EA (1:1), Rf=0.83, IR (nujol): 3279 (NH), 1732, 1699 and 1678 (C=O), 1630 and 1520 (C=C) cm$^{-1}$; $^1$H-NMR: 7.50-7.10 (m); 6.98 (dd); 6.49 (dd); 5.10 (d); 4.52 (d); 3.40 (d); 1.90 (m); 1.7-1.4 1.34 (m).

EXAMPLE 20

1-(Adamantylmethyl-2,4-dioxo-3-[3-(N,N-dimethylamino)phenyloxycarbonylamino]-5-phenyl-2,3,4,5-tetrahydro-1H-1,5-benzodiazepine Pyridine (0.058 ml) and 3-(N,N-dimethylamino)phenyl chloroformate (0.144 g) were added to a solution of the intermediate 47 (0.150 g) in dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a foam. This material was triturated with ethyl ether to give the title compound as a pink solid (0.08 g). M.p. 130°–2°. T.l.c. CH-EA (7:3), Rf=0.38. IR (nujol): 1738, 1709 and 1676 (C=O) cm$^{-1}$; $^1$H-NMR: 7.55-7.24 (m); 7.22-7.11 (m); 6.97 (m); 6.56-6.48 (m); 6.46 (d); 5.13 (d); 4.52 (d); 3.40 (d); 2.92 (s); 1.91 (m); 1.70-1.51 (m); 1.51-1.34 (m).

EXAMPLE 21

1-(Adamantylmethyl)-2,4-dioxo-7-fluoro-3-phenyloxycarbonylamino-5-phenyl-2,3,4,5-tetrahydro-1H-1,5-benzodiazepine Pyridine (0.025 ml) and phenyl chloroformate (0.040 ml) were added to a solution of the intermediate 51 (0.077 g) in dichloromethane (5 ml) under a nitrogen atmosphere. The resulting solution was stirred at 23° for 30 min., then diluted with DCm, washed with a 5% solution of hydrochloric acid (20 ml), a 5% solution of sodium hydrogen carbonate (20 ml) and brine (20 ml). The organic layer was dried and concentrated in vacuo to a yellow oil which was triturated with ethyl ether to give the title compound (0.091 mg) as a white solid. M.p. 156°–9°. T.l.c. CH-EA (2:1), Rf=0.40. IR (nujol): 1693, 1674 (C=O) cm$^{-1}$; $^1$H-NMR: 7.50-7.00 (m); 6.68 (dd); 6.48 (d); 5.10 (d); 4.53 (d); 3.31 (dm); 1.90 (s); 1.75-1.00 (m).

EXAMPLE 22

1-(Adamantylmethyl)-2,4-Dioxo-7-fluoro-3-[3-(N,N-dimethylamino)phenyloxycarbonylamino]-5-[4H-1,5-benzodiazepine Pyridine (0.030 ml) and 3-(N,N-dimethylamino) phenyl chloroformate (0.0738) were added to a solution of the intermediate 56 (0.0828) in dichloromethane (8 ml) under a nitrogen atmosphere. The resulting solution was stirred at 23° for 30 min., then diluted with DCM (10 ml), washed with a 5% solution of hydrochloric acid (30 ml), a 5% solution of sodium hydrogen carbonate (30 ml) and brine (30 ml). The organic layer was dried and concentrated in vacuo to give a brown oil (146 mg) which was triturated with ethyl ether to give the title compound as a brown solid (0.0498). M.p. 242°–3°. T.l.c. CH-EA (2:1), Rf=0.33. IR (nujol): 3283 (NH), 1730, 1701 and 1682 (C=O), 1610 (C=C)cm$^{-1}$; $^1$H-NMR: 7.10-7.00 (m); 6.65 (dd); 6.56-6.45 (m); 6.43 (d); 5.11 (d); 4.53 (d); 3.30 (d); 2.93 (s) 1.91 (bs); 1.70-1.34 (m).

EXAMPLE 23

1-(Adamantylmethyl)-2,4-Dioxo-7-fluoro-3-[3-N,N-dimethylamino)phenyloxycarbonylamino]-5-phenyl-2,3,4,5-tetrahydro-1H-1,5-benzodiazepine Pyridine (0.027 ml) and 3-(N,N-dimethylamino) phenyl chloroformate (0.0658) were added to a solution of the intermediate 51 (0.0708) in dichloromethane (15 ml) under a nitrogen atmosphere. The resulting solution was stirred at 23° for 30 min., then diluted with DCM (15 ml), washed with a 5% solution of hydrochloric acid (30 ml), a 5% solution of sodium hydrogen carbonate (30 ml) and brine (30 ml). The organic layer was dried and concentrated in vacuo to give a brown solid (0.0718). M.p. 239°–41°. T.l.c. CH-EA (2:1), Rf=0.37. IR (nujol): 3294 (NH), 1730, 1701 and 1682 (C=O), 1610 (C=C) cm$^{-1}$; $^1$H-NMR; 7.50-7.14 (m); 7.016 (m); 6.67 (dd); 6.60-6.46 (m); 6.43 (d); 5.12 (d); 4.53 (d); 3.30 (d); 2.92 (s); 1.91 (bs); 1.70-1.34 (m).

EXAMPLE 24

8-Chloro-3-[3-(N,N-dimethylamino)phenyloxycarbonylamino]-2,4-dioxo-1-(3-methylbut-1-yl)-5-phenyl-2,3,4,5-tetrahydro-1H-1,5-benzodiazepine Pyridine (0.065 ml) and 3-(N,N-dimethylamino)phenyl chloroformate (0.168) were added to a solution of the intermediate 60 (0.158) in dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a foam. This material was purified by flash chromatography (eluting with CH-EA 6:4) to a residue which was triturated with diethyl ether to give the title compound as a beige solid (0.10 g). M.p. 199°–200°. T.l.c. CH-EA (1:1), Rf=0.80. IR (nujol): 1732, 1707 and 1682 (C=O) cm$^{-1}$; $^1$H-NMR: 7.48-7.3 (m); 7.24-7.14 (m); 6.932 (d); 6.58-6.48 (m); 6.4 18 (d); 5.123 (d); 4.566 (m);

3.662 (m); 2.928 (s); 1.6-1.4 (m); 0.942 (s); 0.922 (d).

EXAMPLE 25

7,8-Dichloro-2,4-dioxo-3-(3-methoxyphenyloxycarbonyl)amino-1-(3-methyl-1-butyl)-5-phenyl-2,3,4,5-tetrahydro-1H-1,5-benzodiazepine Pyridine (0.04 ml) and phenyl chloroformate (0.077 g) were added to a solution of the intermediate 30 (0.10 g) in dry dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a solid which was triturated with diethyl ether to give the title compound as a white solid (0.08 g). M.p. 205°–6°. T.l.c. CH-EA (7:3), Rf=0.69. IR (nujol): 3300 (NH), 1734, 1711 and 1690 (C=O) cm$^{-1}$; $^1$H-NMR: 7.55 (s); 7.46 (t); 7.42-7.13 (m); 7.08 (m); 6.43 (d); 5.10 (d); 4.63-4.58 (m); 1.57 (m); 1.52-1.44 (m); 0.92-0.90 (dd).

EXAMPLE 26

7,8-Dichloro-2,4-dioxo-3-(3-methoxyphenyloxycarbonyl)amino-1-(3-methyl-1-butyl)-5-phenyl-2,3,4,5-tetrahydro-1H-1,5-benzodiazepine Pyridine (0.04 ml) and 3-methoxyphenyl chloroformate (0.092 g) were added to a solution of the intermediate 30 (0.10 g) in dry dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to an oil which was purified by flash chromatography (eluting with CH-EA 8:2) to give a pale yellow solid (0.1 g). The latter was further purified by trituration with diethyl ether/petroleum to give the title compound as a white solid (0.068). M.p. 139°–140°. T.l.c. CH-EA (723), Rf=0.63, IR (nujol): 3300 (NH), 1732, 1709 and 1690 (C=O) cm$^{-1}$; $^1$H-NMR 7.55 (s); 7.46 (m); 7.39 (m); 7.24 (t); 7.18 (m); 7.08 (s); 6.74 (m); 6.42 (d); 5.09 (d); 4.57 (m); 3.62 (m); 3.78 (s); 1.62-1.44 (m); 0.94 (d); 0.92 (d).

EXAMPLE 27

3-(3-Bromophenyloxycarbonyl)amino-7,8-dichloro-2,4-dioxo-1-(3-methyl-1-butyl)-5-phenyl-2,3,4,5-tetrahydro-1H-1,5-benzodiazepine Pyridine (0.04 ml) and 3-bromophenyl chloroformate (0.1168) were added to a solution of the intermediate 30 (0.10 g) in dry dichloromethane (10 ml) under a nitrogen atmosphere. The resulting solution was stirred at 23° for 1 h, then washed with a 5% solution of hydrochloric acid (20 ml), a 5% solution of sodium hydrogen carbonate (20 ml) and brine (20 ml). The organic layer was dried and concentrated in vacuo to a residue which was triturated with diethyl ether/petroleum to give the title compound as a white solid (0.0698). M.p. 163°–2°. T.l.c. CH-EA (723), Rf=0.67. IR (nujol): 3244 (NH), 1709 and 1682 (C=O) cm$^{-1}$; $^1$H-NMR: 7.56 (s); 7.47 (m); 7.39 (m); 7.36-7.30 (m); 7.22 (t); 7.18 (m); 7.10 (m); 7.08 (s); 6.45 (d); 5.07 (d); 4.58 (m); 3.63 (m); 1.64-1.44 (m); 0.95 (d); 0.92 (d).

EXAMPLE 28

7,8-Dichloro-2,4-dioxo-3-[(3-methoxycarbonyl)phenyloxycarbonyl]amino-1-(3-methyl-1-butyl)-5phenyl-2,3,4,5-tetrahydro-1H-1,5-benzodiazepine Pyridine (0.04 ml) and 3-methoxycarbonylphenyl chloroformate (0.3178) were added to a solution of the intermediate 30 (0.10 g) in dry dichloromethane (10 ml) under a nitrogen atmosphere. The resulting solution was stirred at 23° for 30 mm, then washed with a 5% solution of hydrochloric acid (20 ml), a 5% solution of sodium hydrogen carbonate (20 ml) and brine (20 ml). The organic layer was dried and concentrated in vacuo to a residue which was triturated with diethyl ether to give the title compound as a white solid (0.2568). M.p. 179°–80° C. T.l.c. CH-EA (7:3), Rf=0.5. IR (nujol): 1730, 1717 and 1682 (C=O) cm$^{-1}$; $^1$H-NMR: 7.89 (m); 7.83 (t); 7.56 (s); 7.51-7.34 (m); 7.19 (d); 7.08 (s); 6.48 (d); 5.09 (d); 4.58 (m); 3.90 (s); 3.63 (m); 1.57 (m); 1.52-1.44 (m); 0.95 (d); 0.93 (d).

EXAMPLE 29

(+)-2,4-Dioxo-1-(3-methyl-1-butyl)-5-phenyl-3-phenyloxycarbonylamino-2,3,4,5-tetrahydro-1H-1,5-benzodiazepine Pyridine (0.1 ml) and phenyl chloroformate (0.16 ml) were added to a solution of the intermediate 66 (0.208) in dichloromethane (10 ml) under a nitrogen atmosphere. The resulting solution was stirred at 23° for 30 mm, then concentrated in vacuo to a residue which was purified by flash chromatography (eluting with CH-EA 8:2) to give the title compound as a white foam (0.158). M.p. 70°. T.l.c. CH-EA (8:2), Rf=0.46. [alpha]D=+125.9 (CHCl$_3$; c=0.835).

EXAMPLE 30

(+)-2,4-Dioxo-3-(3-methoxyphenyloxycarbonyl)amino-1-(3-methyl-1-butyl)-5-phenyl-2,3,4,5-tetrahydro-1H-1,5-benzodiazepine Pyridine (0.052 ml) and 3-methoxyphenyl chloroformate (0.121 g) were added to a solution of the intermediate 66 (0.10 g) in dry dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a residue which was purified by flash chromatography (eluting with CH-EA 2:1) to give the title compound as a white foam (0.0678). T.l.c. CH-EA (2:1), Rf=0.39. [alpha]D=+103.9 (CHCl$_3$; c=0.92).

EXAMPLE 31

(+)-3-(3-Bromophenylcarbonyl)amino-2,4-dioxo-1-(3-methyl-1-butyl)-5-phenyl-2,3,4,5-tetrahydro-1H-1,5-benzodiazepine Pyridine (0.052 ml) and 3-bromophenyl chloroformate (0.154 g) were added to a solution of the intermediate 66 (0.10 g) in dry dichloromethane (10 ml) under a nitrogen atmosphere. The resulting solution was stirred at 23° for 1 h, then washed with a 5% solution of hydrochloric acid (20 ml), a 5% solution of sodium hydrogen carbonate (20 ml) and brine (30 ml). The organic layer was dried and concentrated in vacuo to a residue which was purified by flash chromatography (eluting with CH-EA 2:1) to give the title compound as a white foam (0.07 g). T.l.c. CH-EA (2:1), Rf=0.53. [alpha]D=+91.6 (CHCl$_3$; c=1.15).

EXAMPLE 32

1-(2,2-dimethyl-ethoxycarbonyl)methyl-2,4-dioxo-5-phenyl-3-phenyl-oxycarbonylamino-2,3,4,5-tetrahydro-1H-1,5-benzodiazepine Pyridine (0.017 ml) and phenyl chloroformate (0.026 ml) were added to a solution of the intermediate 69 (0.040 g) in dichloromethane (10 ml) under a nitrogen atmosphere. The resulting solution was stirred at 23° for 1 h, then washed with a 5% solution of hydrochloric acid (15 ml), a 5% solution of sodium hydrogen carbonate (15 ml) and brine (20 ml). The organic layer was dried and concentrated in vacuo to a solid which was triturated with diethyl ether/petroleum (2/8) to give the title compound as a white solid (0.010). T.l.c. CH-EA (1:1), Rf=0.64. IR (nujol): 1740, 1701 and 1686 (c=O) cm$^{-1}$; $^1$H-NMR: 7.5-7.1 (m); 7.013 (d); 6.466 (d); 5.226 (d); 4.806 (d); 4.451 (d); 1.448 (s).

EXAMPLE 33

1-(adamantylmethyl);2,4-dioxo-3-(3-methoxycarbonyl)phenyloxycarbonylamino-5-phenyl-2,3,4,5-tetrahydro-1H-1,5-benzodiazepine Pyridine (0.161 ml) and 3-(methoxycarbonyl)phenylchloroformate (0.429 g) in dichloromethane (1 ml) were added to a solution of the intermediate 47 (0.415 g) in dry dichloromethane (10 ml) under a nitrogen atmosphere. The resulting solution was stirred at 23° for 45 min, then diluted with dichloromethane (10 ml), washed with a 5% solution of hydrochloric acid (20 ml), a 5% solution of sodium hydrogen carbonate (20 ml) and brine (30 ml). The organic layer was dried and concentrated in vacuo to a foam (0.695 g). This material was triturated with diethylether/petroleum (1/5) to give a white solid (0.500 g). This material was purified by flash chromatography on silica gel, eluting CH/EA 2/1 and the solid obtained (0.3948) was triturated with diethylether/petroleum 1/5 (18 ml), to give the title compound as a white solid (0.305 g). M.p. 197°∝199°. T.l.c. CH-EA (2:1), R.f=0.40. IR (nujol): 1734, 1722, 1700 and 1676 (c=O) cm$^{-1}$; $^1$H-NMR: 7.88 (d); 7.50 (m); 7.47-7.40 (m); 7.40-7.34 (m); 7.30 (m); 7.18 (m); 6.99 (dd); 7.83 (t); 6.54 (d); 5.09 (d); 4.53 (d); 3.40 (d); 3.90 (s): 1.90 (m); 1.65 (m); 1.58-1.35 (m).

EXAMPLE 34

1-(adamantylmethyl)-2,4-dioxo-3-(3-carboxy)phenyl-oxycarbonylamino-5-phenyl-2,3,4,5-tetrahydro-1H-1,5-benzodiazepine Aluminium iodide (0.506 g) was added to a solution of the Example 33 (0.1408) in dry acetonitrile (15 ml) under a nitrogen atmosphere. The resulting suspension was stirred at 80° for 4 h, then the solvent was evaporated and the residue taken up in dichloromethane (25 ml), washed with a 5% solution of sodium thiosulfate (20 ml), a 10% solution of hydrochloric acid (3×30 ml), a 5% solution of sodium hydrogen carbonate (25 ml), 10% solution of Potassium sodium tanrate tetrahydrate (2×20 ml) and brine (2×30 ml). The organic layer was dried and concentrated in vacuo to a foam (0.1068). This material was purified by flash chromatography on silica gel, eluting with DCM, increasing polarity to DCM/Methanol 95/5 to 80/20 to give the title compound as a white solid (0.045 g). T.l.c. EA, Rf=0.42 IR (nujol): 3430 (NH), 1709, 1684 (c=O) cm$^-$; $^1$H-NMR: 8.08 (d); 7.83 (d); 7.75 (d); 7.58 (bs); 7.513 (t); 7.45-7.3 (m); 7.265 (t); 7.162 (bd); 6.94 (dd); 5.009 (d); 4.328 (d); 3.63 (d); 1.865 (bs); 1.56 (m); 1.369 (m).

EXAMPLE 35

7,8-Dichloro-2,4-dioxo-1-[(3-methyl-2-oxo)-but-1-yl]-5-phenyl-3(phenyloxycarbonyl)amino-2,3,4,5-tetrahydro-1H-1,5-benzodiazepine Pyridine (0.015 ml) and phenylchloroformate (0.025 g) were added to a solution of the intermediate 75 (0.04 g) in dichloromethane (4 ml) under a nitrogen atmosphere. The resulting solution was stirred at 23° for 1 h, then diluted with dichloromethane (25 ml), washed with a 5% solution of hydrochloric acid (30 ml), a 5% solution of sodium hydrogen carbonate (30 ml) and brine (30 ml). The organic layer was dried and concentrated in vacuo to a foam (0.72 g) purified by flash chromatography (eluting with CH/EA 8/2) to give the title compound as a white solid (0.042 g). M.p. 130°–2°. T.l.c. CH-EA, 6/4 Rf=0.66. IR (nujol): 3425 (NH), 1715, 1686 (c=O) cm$^{-1}$; $^1$H-NMR: 7.35 (s); 7.52-7.12 (m); 7:09 (s); 6.41 (d); 5.21 (d); 5.14 (d); 4.63 (d); 2.75 (m); 1.21 (d); 1.20 (d).

EXAMPLE 36

3-[3-Bromo-phenyloxycarbonylamino-7,8-dichloro-2,4-dioxo-1-[(3-methyl-2-oxo)but-1-yl]-5-phenyl-2,3,4,5-tetrahydro-1H-1,5-benzodiazepine Pyridine (0.015 ml) and 3-bromo-phenylchloroformate (0.035 g) were added to a solution of the intermediate 75 (0.031 g) in dichloromethane (4 ml) under a nitrogen atmosphere. The resulting solution was stirred at 23° for 1 h, then a further amount of pyridine (0.005 ml) and 3-bromo-phenylchloroformate (0.005 g) were added and stirring continued for 1 h. The reaction mixture was then diluted with dichloromethane (30 ml), washed with a 5% solution of hydrochloric acid (30 ml), a 5% solution of sodium hydrogen carbonate (30 ml) and brine (30 ml). The organic layer was dried and concentrated in vacuo to a foam which was triturated with diethyl ether to give the crude compound (0.075 g) which was purified by flash chromatography (eluting with CH/EA 8/2) to give the title compound (0.040 g),. M.p. 204°–5°. T.l.c. CH-EA 6/4 Rf=0.70 IR (nujol): 3425 (NH), 1715 (C=O) cm$^{-1}$; $^1$H-NMR: 7.35 (s); 7.54-7.30 (m); 7.21 (t); 7.11 (m); 7.10 (s); 6.42 (d); 5.18 (d); 5.14 (d); 4.63 (d); 2.76 (m); 1.22 (d); 1.20 (d).

EXAMPLE 37

8-Chloro-2,4-dioxo-1-(3-methyl-1-butyl)-3-phenyloxycarbonylamino-5-phenyl-2,3,4,5-tetrahydro-1H-1,5-benzodiazepine Pyridine (0.032 ml) and phenyl chloroformate (0.05 ml) were added to a solution of the intermediate 83 (0.076 g) in dichloromethane (7 ml) under a nitrogen atmosphere. The resulting solution was stirred at 23° for 30 min, then washed with a 5% solution of hydrochloric acid (10 ml), a 5% solution of sodium hydrogen carbonate (10 ml) and brine (2×10 ml). The organic layer was dried and concentrated in vacuo to a residue which was triturated with diethyl ether to give the title compound as a white solid (0.054 g). M.p. 190°–5°. T.l.c. CH-EA (6:4), Rf=0.63, IR (nujol): 1732, 1713 and 1664 (c=O) cm$^4$; $^1$H-NMR: 7.48-7.40 (m); 7.38-7.32 (m); 7.22-7.14 (m); 6.94 (d); 6.46 (d); 5.11 (d); 4.57 (m): 3.67 (m); 1.57-1.49 (m); 0.93 (d); 0.91 (d).

EXAMPLE 38

8-Chloro-2,4-dioxo-3-(3-methoxyphenyloxycarbonyl)amino-1-(3-methyl-1-butyl)-5-phenyl-2,3,4,5-tetrahydro-1H-1,5-benzodiazepine Pyridine (0.047 ml) and 3-methoxyphenyl chloroformate (0.11 g) were added to a solution of the intermediate 83 (0.10 g) in dry dichloromethane (10 ml) under a nitrogen atmosphere. The resulting solution was stirred at 23° for 30 min, then washed with a 5% solution of hydrochloric acid (20 ml), a 5% solution of sodium hydrogen carbonate (20 ml) and brine (20 ml). The organic layer was dried and concentrated in vacuo to a residue which was triturated with diethyl ether/cyclohexane to give the title compound as a white solid (0.07 g). M.p. 129°-30°. T.l.c. CH-EA (7:3), Rf=0.55. IR (nujol): 3312 (NH), 1734, 1695 and 1678 (c=O) cm$^{-1}$; $^1$H-NMR: 7.5-7.3 (m); 7.2-7.1 (m); 6.94 (d); 6.8-6.76 (m): 6.72 (t); 6.44 (d); 5.10 (d); 4.57 (m); 3.66 (m); 3.78 (s); 1.6-1.4 (m); 0.94 (d); 0.92 (d).

EXAMPLE 39

3-(3-Bromophenyloxycarbonyl)amino-8-chloro-2,4-dioxo-1-(3-methyl-1-butyl)-5-phenyl-2,3,4,5-tetrahydro-1H-1,5-benzodiazepine Pyridine (0.047 ml) and 3-bromophenyl chloroformate (0.14 g) were added to a solution of the intermediate 83 (0.10 g) in dry dichloromethane (10 ml) under a nitrogen atmosphere. The resulting solution was stirred at 23° for 1 h, then washed with a 5% solution of hydrochloric acid (20 ml), a 5% solution of sodium hydrogen carbonate (20 ml) and brine (20 ml). The organic layer was dried and concentrated in vacuo to a residue which was triturated with cyclohexane to give the title compound as a white solid (0.1 g). M.p. 144°-5°. T.l.c. CH-EA (7:3), Rf=0.63, IR (nujol): 3400 CNH), 1732, 1707 and 1680 (c=O) cm$^{-1}$; $^1$H-NMR: 7.50-7.30 (m); 7.21-7.1 (m); 6.94 (d); 6.47 (d); 5.07 (d); 4.57 (m); 3.67 (m); 1.66-1.4 (m); 0.94 (d); 0.93 (d).

EXAMPLE 40

2,4-Dioxo-8-fluoro-1-(3-methyl-1-butyl)-5-phenyl-3-phenyloxycarbonylamino-2,3,4,5-tetrahydro-1H-1,5-benzodiazepine Pyridine (0.04 ml) and phenyl chloroformate (0.07 ml) were added to a solution of the intermediate 87 (0.10 g) in dichloromethane (10 ml) under a nitrogen atmosphere. The resulting solution was stirred at 23° for 30 min, then washed with a 5% solution of hydrochloric acid (10 ml), a 5% solution of sodium hydrogen carbonate (10 ml) and brine (10 ml). The organic layer was dried and concentrated in vacuo to a solid which was triturated with diethyl ether to give the title compound as a white solid (0.07 g). M.p. 160°-5°. T.l.c. CH-EA (6:4), Rf=0.58. IR (nujol): 3292 (NH), 1730, 1713 and 1670 (c=O) cm$^{-1}$; $^1$-NMR: 7.43 (m); 7.38-7.30 (m); 7.22-7.12 (m); 7.03-6.90 (m); 6.46 (d); (d); 4.57 (m); 3.66 (m); 1.66-1.40 (m); 0.95 (d); 0.92 (d).

EXAMPLE 41

2,4-Dioxo-1-(3-hydroxy-1-propyl)-5-phenyl-3-(phenyloxycarbonylamino)-2,3,4,5-tetrahydro-1H-1,5-benzodiazepine Pyridine (0.049 ml) and phenyl chloroformate (0.077 ml) were added to a solution of the intermediate 79 (0.1 g) in dichloromethane (10 ml) under a nitrogen atmosphere. The resulting solution was stirred at 23° for 20 mm, then washed with a 5% solution of hydrochloric acid (20 ml), a 5% solution of sodium hydrogen carbonate (20 ml) and brine (20 ml). The organic layer was dried and concentrated in vacuo to an oil, which was purified by flash chromatography (eluting in gradient from CH-EA 1:1to CH-EA 2:8) to give the title compound as a white solid (0.06 g). M.p. 203°-4°. T.l.c. CH-EA (20:80), Rf=0.25. IR (nujol): 1728, 1690 and 1668 (C=O) cm$^{-1}$; $^1$H-NMR: 7.51 (d); 7.5-7.1 (m); 7.00 (d); 6.48 (d); 5.17 (d); 4.66 (m); 3.92 (m); 7-3.46 (m); 2.32 (t); 2.0-1.71 (m).

Pharmacy Example

| Capsules or Tablets | mg/dosage form |
|---|---|
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Sulphate | 1.0 |
| | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| Active ingredient | 0.1 |
|---|---|
| Povidone | 15.4 |
| Lactose | 74.0 |
| Hydrogenated vegetable oils | 3.0 |
| Silicon dioxide | 1.0 |
| Sodium Lauryl sulphate | 1.5 |
| Crospovidone | 5.0 |
| | 100.0 |

The active ingredient is dispersed in a suitable solvent (e.g. ethanol) together with povidone. The solution is sprayed on to lactose and the solvent removed. The powder obtained is blended with the other excipients. The blend is used to fill gelatine capsules or compressed using appropriate punches. The tablet can be coated using conventional techniques and coatings.

| Oral liquid | |
|---|---|
| Active ingredient | 70–100 micrograms/dose |
| ethanol | 5–15% |
| Sodium saccharinate | 0.1–1% |
| Propylene glycol | q.b. 100% |
| Injection Formulation | |
| Active ingredient | 0.1–100 microgramms |
| Sodium phosphate | 1.50 mg/ml |

-continued

| | |
|---|---|
| NaOH | qs desired pH (range 3–9) |
| glyerol | 10–500 mg/ml |
| water for injection | qs to 0.5–10 ml |

Pack in glass (ampules) with a rubber stopper (vials, syringes) and a plastic/metal overseal (vials only). An inert gas atmosphere (for example nitrogen) may be introduced into dead space of container.

CCK—Antagonist Activity

The CCK-A antagonist and CCK-B antagonist activities of compounds of the invention may be determined using the guinea pig isolated ileum longitudinal muscle myenteric plexus preparation and the procedure G Dal Forno et al *J. Pharmacol. Exp & Ther.* 261—1056–1063 1992.

CCK—Receptor Binding

The binding affinity of the compounds of the invention for the CCK-A receptor (Pancreas Assay) and CCK-B receptor (guinea pig cortex assay) was determined using the procedure of G Dal Forno et al *J. Pharmacol. Exp & Ther.* 261—1056–1063. The pKi values determined with representative compounds of invention were as follows:

| | pKi | |
|---|---|---|
| Compound Ex No | CCK-A | CCK-B |
| 1 | 5.29 | 7.67 |
| 3 | 6.24 | 8.50 |
| 4 | 6.25 | 8.51 |
| 7 | 6.43 | 8.41 |
| 8 | 6.38 | 8.80 |
| 9 | 6.75 | 8.99 |
| 12 | 5.49 | 8.13 |
| 13 | 6.25 | 8.34 |
| 20 | 5.48 | 7.91 |
| 24 | 5.89 | 8.47 |
| 25 | 5.37 | 8.20 |
| 38 | 5.35 | 7.70 |

The compounds of the invention are essentially non-toxic and therapeutically useful doses.

We claim:

1. A compound of general formula (I)

wherein $R^1$ represents a phenyl, $C_{3-7}$cycloalkyl, bridged $C_{7-11}$cycloalkyl or $C_{1-6}$alkyl group which alkyl group may be substituted by a hydroxy, phenyl, $C_{1-6}$alkoxycarbonyl, $C_{3-7}$cycloalkyl or bridged $C_{7-11}$cycloalkyl group or $R^1$ represents the group $XYR^4$ wherein X is a $C_{1-3}$ straight or branched alklene chain, Y is C=O, $C(OR^5)_2$ or $C(SR^5)$ and is a $R^4$ is a $C_{1-6}$alkyl, optionally substituted phenyl, $C_{3-7}$cycloalkyl or bridged $C_{7-11}$-cycloalkyl.

$R^2$ represents a substituted or unsubstituted phenyl (wherein the substitutents may be 1 or 2 of halo, $C_{1-4}$alkyl, nitro, cyano, trifluoromethyl, trifluoromethoxy $C_{1-4}$alkylthio or $(CH_2)_n R^6$ wherein $R^6$ is hydroxy, $C_{1-4}$alkoxy, $CO_2R^7$ or $NR^8R^9$.

$R^3$ represents phenyl optionally substituted by one or two halogen atoms;

$R^7$ represents hydrogen or a $C_{1-1}$alkyl group;

$R^8$ and $R^9$ independently represent hydrogen or a $C_{1-4}$alkyl group.

$R^{10}$ represents hydrogen or a halogen atom; m is zero, 1 or 2;

n is zero or 1; pharmaceutically acceptable salts and solvates thereof.

2. A compound as claimed in claim 1 wherein $R^1$ represents a bridged $C_{7-10}$cycloalkyl, $C_{4-6}$alkyl, $C_{3-6}$hydroxy alkyl, $C_{1-2}$alkyl substituted by a bridged $C_{7-10}$cycloalkyl group $C_{2-3}$alkyl substituted by $C_{3-7}$cycloalkyl or the group $CH_2COR^4$ in which $R^4$ is $C_{3-4}$alkyl.

3. A compound as claimed in claim 1 wherein $R^1$ is 3-methylbutyl 3,3-dimethylbutyl, adamantylmethyl, $CH_2COCH(CH_3)_2$, or cyclopentylethyl.

4. A compound as claimed in claim 1 wherein $R^2$ represents phenyl optionally substituted by chlorine, fluorine, bromine, methyl, methoxy, dimethylamino or $(CH_2)$; $CO_2R^7$ wherein $R^7$ is hydrogen methyl or ethyl.

5. A compound as claimed in claim 1 wherein $R^2$ represents phenyl optionally substituted by dimethylamino, methoxy, bromine, carboxyl or methoxycarbonyl.

6. A compound as claimed in claim 1 wherein $R^3$ represents phenyl or phenyl substituted by fluorine, in the ortho and/or para position.

7. A compound as claimed in claim 1 wherein $R^{10}$ is hydrogen, chlorine or fluorine.

8. A compound as claimed in claim 1 wherein $R^1$ is 3-methylbutyl $R^2$ is phenyl optionally substituted in the meta position by dimethylamino, methoxy, bromine, methoxycarbonyl or carboxyl; $R^3$ is phenyl or orthofluorophenyl, $R^{10}$ is chloro or fluorine at the 8 position or $R^{10}$ is chlorine at 7 and 8 positions or $R^{10}$ is hydrogen.

9. A compound as claimed in claim 1 having the configuration 10. 8-Chloro-2,4-dioxo-1-(3-methyl-1-butyl)-3-phenyloxycarbonylamino- 5-phenyl-2,3,4,5-tetrahydro-1H-1,5-benzodiazepine; 7,8-Dichloro-3-[3-(N,N-dimethylamino)phenyloxycarbonylamino]-2,4-dioxo-1-(3-methylbut-1-yl)-5-phenyl-2,3,4,5-tetrahydro-1H-1,5-benzodiazepine; 8-Chloro-3-[3-(N,N-dimethylamino)phenyloxycarbonylamino]-2,4-dioxo-(3-methylbut-1-yl)-5-phenyl-2,3,4,5-tetrahydro-1H-1,5-benzodiazepine; 8-Chloro-2,4-dioxo-3-(3-methoxyphenyloxycarbonyl)amino-1-(3-methyl-1-butyl)-5-phenyl-2,3,4,5-tetrahydro-1H-1,5-benzodiazepine; 3-(3-Bromophenyloxycarbonyl)amino-8-chloro-2,4-dioxo-1-(3-methyl-1-1-butyl)-5-phenyl-2,3,4,5-tetrahydro-1H-1, 5-benzodiazepine; 1-(Adamantylmethyl)-2,4-dioxo-3-[3-(N,N-dimethylamino)phenyloxycarbonylamino]-5-phenyl-2,3,4,5-tetrahydro-1H-1,5-benzodiazepine; 3-[3-(N,N-dimethylamino)phenyloxycarbonylamino]-2,4-dioxo-5-(2-fluorophenyl)-1-(3-methylbut-1-yl)-2,3,4,5-tetrahydro-1H-1,5-benzodiazepine; 2,4-Dioxo-1-(3-methylbut-1-yl)-5-phenyl-3-(phenyloxycarbonylamino)-2,3,4,5-tetrahydro-1H-1,5-benzodiazepine and the (+) enenatiomers thereof.

11. A composition for treating central nervous disorders or anxiety disorders comprising a compound as claimed in claim 1 in admixture with one or more physiologically acceptable carriers or excipients.

12. A method of treatment of a mammal including man for conditions where modification of the effects of gastrin and or CCK is a therapeutic benefit comprising administration of an effective amount of a compound as claimed in any of claim 1.

13. A method of treatment of a mammal including man for central nervous disorders, which comprises administrating an effective amount of the compound of claim 1, to a mammal.

14. A method of treatment of a mammal including man for anxiety disorders, which comprises administrating an effective amount of the compound of claim 1, to a mammal.

* * * * *